US012644142B2

(12) United States Patent
Yasuda et al.

(10) Patent No.: US 12,644,142 B2
(45) Date of Patent: Jun. 2, 2026

(54) SUGAR COMPOSITION CONTAINING CYCLIC TETRASACCHARIDE, USE THEREOF, AND PRODUCTION METHOD THEREFOR

(71) Applicant: NAGASE VIITA CO., LTD., Okayama (JP)

(72) Inventors: Akiko Yasuda, Okayama (JP); Manabu Miyata, Okayama (JP); Takuo Yamamoto, Okayama (JP); Akiko Mizote, Okayama (JP); Hitoshi Mitsuzumi, Okayama (JP)

(73) Assignee: NAGASE VIITA CO., LTD., Okayama (JP)

( * ) Notice: Subject to any disclaimer, the term of this patent is extended or adjusted under 35 U.S.C. 154(b) by 864 days.

(21) Appl. No.: 17/766,405

(22) PCT Filed: Oct. 2, 2020

(86) PCT No.: PCT/JP2020/037581
§ 371 (c)(1),
(2) Date: Apr. 4, 2022

(87) PCT Pub. No.: WO2021/066159
PCT Pub. Date: Apr. 8, 2021

(65) Prior Publication Data
US 2023/0242957 A1      Aug. 3, 2023

(30) Foreign Application Priority Data
Oct. 4, 2019      (JP) ................................. 2019-183875

(51) Int. Cl.
| | |
|---|---|
| *C12P 19/16* | (2006.01) |
| *A23L 29/30* | (2016.01) |
| *C07H 3/06* | (2006.01) |
| *C12N 9/10* | (2006.01) |
| *C12N 9/34* | (2006.01) |
| *C12N 9/44* | (2006.01) |
| *C12P 19/14* | (2006.01) |

(52) U.S. Cl.
CPC .............. *C12P 19/16* (2013.01); *A23L 29/30* (2016.08); *C07H 3/06* (2013.01); *C12N 9/1074* (2013.01); *C12N 9/2428* (2013.01); *C12N 9/2457* (2013.01); *C12P 19/14* (2013.01); *C12Y 302/0102* (2013.01)

(58) Field of Classification Search
CPC ............ C12P 19/16; C12P 19/14; C12P 19/00
See application file for complete search history.

(56) References Cited

U.S. PATENT DOCUMENTS

| | | | | |
|---|---|---|---|---|
| 2003/0194762 | A1 | 10/2003 | Kubota et al. | |
| 2004/0236097 | A1* | 11/2004 | Aga ....................... | A61Q 19/00 |
| | | | | 536/123 |
| 2004/0254367 | A1 | 12/2004 | Oku et al. | |
| 2005/0009017 | A1 | 1/2005 | Kubota et al. | |
| 2005/0267067 | A1 | 12/2005 | Oku et al. | |
| 2006/0210646 | A1 | 9/2006 | Oku et al. | |
| 2006/0276432 | A1 | 12/2006 | Oku et al. | |
| 2009/0048188 | A1 | 2/2009 | Matsuo et al. | |

FOREIGN PATENT DOCUMENTS

| | | |
|---|---|---|
| JP | 2006-206502 A | 8/2006 |
| WO | 2001/090338 A1 | 11/2001 |
| WO | 2002/010361 A1 | 2/2002 |
| WO | 2002/072594 A1 | 9/2002 |
| WO | 2003/044032 A1 | 5/2003 |

(Continued)

OTHER PUBLICATIONS

Watanabe, H. et al., "Enzymatic synthesis of a 2-0-et-D-glucopyranosyl cyclic tetrasaccharide by kojibiose phosphorylase", Carbohydrate Research 2005, vol. 340, pp. 449-454.

Aga, H. et al., Lecture abstracts of the conference of the Society for Biotechnology, Japan, Aug. 25, 2003, p. 54, [2A 14-1], along with its English translation by the applicant.

Aga, H. et al., "Production of Cyclic Tetrasaccharide from Starch Using a Novel Enzyme System from Bacillus globisporus C11", Journal of Bioscience and Bioengineering 2002, vol. 94, No. 4, pp. 336-342.

(Continued)

*Primary Examiner* — Layla D Berry

(74) *Attorney, Agent, or Firm* — FISHERBROYLES, LLP; Roger L. Browdy

(57) ABSTRACT

The present invention aims to provide a saccharide composition suitable for a cyclic-tetrasaccharide-containing starch syrup which has low viscosity, low water activity, low coloration property, and low calorie content, and which is unlikely to cause precipitation of crystals of saccharides during storage, and to provide a use of the composition and a production method for the composition. The object is achieved by providing a cyclic-tetrasaccharide-containing saccharide composition having the following characteristics (1) to (3): (1) the saccharide composition includes a branched cyclic tetrasaccharide in addition to the cyclic tetrasaccharide, wherein the content of the cyclic tetrasaccharide with respect to the total solid content of the saccharide composition obtained by allowing glucoamylase and α-glucosidase to act on the above saccharide composition is 38% by mass or higher, on a dry solid basis; (2) the ratio of α-1,4-linked glucose in the total glucose residues constituting the saccharide composition in methylation analysis is over 9% and 15% or lower, and (3) the ratio of α-1,4,6-linked glucose in the total glucose residues constituting the saccharide composition in methylation analysis is less than 6%; and providing a use of the composition and a production method for the composition.

19 Claims, No Drawings

(56) References Cited

FOREIGN PATENT DOCUMENTS

| WO | 2004/020552 | A1 | 3/2004 |
| WO | 2004/089964 | A1 | 10/2004 |
| WO | 2005/007171 | A1 | 1/2005 |

OTHER PUBLICATIONS

Cote, G. L. et al., "Enzymically produced cyclic a-1,3-linked and a-I,6-linked oligosaccharides of D-glucose", European Journal of Biochemistry 1994, vol. 226, No. 2, pp. 641-648.
Oku, T. et al., Luminacoids Research 2018, vol. 22, No. 1, pp. 29-33.

* cited by examiner

SUGAR COMPOSITION CONTAINING CYCLIC TETRASACCHARIDE, USE THEREOF, AND PRODUCTION METHOD THEREFOR

TECHNICAL FIELD

The present invention relates to a novel saccharide composition, more specifically, a novel saccharide composition containing a cyclic tetrasaccharide represented by cyclo{→6)-α-D-glucopyranosyl-(1→3)-α-D-glucopyranosyl-(1→6)-α-D-glucopyranosyl-(1→3)-α-D-glucopyranosyl-(1→}, a use of the composition, and a production method for the composition.

BACKGROUND ART

The cyclic tetrasaccharide having a structure represented by cyclo{→6)-α-D-glucopyranosyl-(1→3)-α-D-glucopyranosyl-(1→6)-α-D-glucopyranosyl-(1→3)-α-D-glucopyranosyl-(1→} (hereinafter simply referred to as "cyclic tetrasaccharide") is a cyclic carbohydrate composed of four glucose molecules, discovered by Cote in 1994 (Non-patent Document 1). Its production method using an enzyme derived from a soil microorganism has been established in the 2000s by the same applicant as the applicant of the present application (Patent Documents 1 and 2). Since cyclic tetrasaccharides have no reducing power and are highly stable because of their structures, their industrial application has been expected. The above establishment of the production method has led to a wide range of intensive studies on their practical application. As a result, for example, low coloration (Patent Documents 1 and 2), low calorie property (Patent Documents 1 and 2), dietary fiber property (Patent Documents 1 and 2), radical production-inhibitory action (Patent Document 3), lipid-regulating action (Patent Document 4), and mineral absorption-promoting action (Patent Document 5) have so far been known as representative actions of cyclic tetrasaccharides. It is thought, according to these discoveries, that, if a cyclic tetrasaccharide or a cyclic-tetrasaccharide-containing saccharide composition can be made widely available in the form of a starch syrup or the like as a food material or the like, the increasing demands for comfort, safety, and health in the modern society can be satisfied.

In general, a starch syrup is obtained by hydrolyzing starch with an enzyme or an acid, purifying the resulting product by decoloration and desalting, and then concentrating the product. Thus, a starch syrup can be produced at relatively low cost, and there is no need to dissolve solid carbohydrate in water during the process of, for example, mixing with other materials to obtain the final product. Therefore, starch syrups have been widely preferably used as materials of food products. Starch syrups are generally required to have, for example, the following properties: (a) its viscosity is not too high; and (b) its water activity is low. The property (a) is required from the viewpoint of avoiding disturbance of the handleability in the process of, for example, mixing with other materials in the production of the final product, and the property (b) is a property required from the viewpoint of avoiding contamination with microorganisms during storage. Further, when use of a starch syrup containing a cyclic tetrasaccharide is taken into account, the starch syrup is required to have, in addition to the properties (a) and (b), the following properties: (c) sufficiently low coloration; and (d) low calorie content; which are advantageous characteristics unique to cyclic tetrasaccharides. Furthermore, of course, the starch syrup is required to have the following property: (e) it does not to cause precipitation of crystals of saccharides during storage even when it is prepared as a highly concentrated aqueous solution (having a solid concentration of, for example, 70% by mass). Although Patent Document 2 and the like disclose a variety of starch syrups containing a cyclic tetrasaccharide, such conventional starch syrups, as far as the present applicant knows, have not been practically applied since they did not reach the levels of the items (a) to (e) required in the food field. There has not even been a technical proposal by which starch syrups satisfying such levels can be provided.

PRIOR ART DOCUMENTS

Patent Documents

[Patent Document 1] International Publication No. WO 2002/010361
[Patent Document 2] International Publication No. WO 2001/090338
[Patent Document 3] International Publication No. WO 2004/020552
[Patent Document 4] International Publication No. WO 2004/089964
[Patent Document 5] International Publication No. WO 2005/007171

Non-Patent Documents

[Non-patent Document 1] European Journal of Biochemistry. vol. 226, pp. 641-648 (1994)
[Non-patent Document 2] Journal of Bioscience and Bioengineering. vol. 94, issue 4, pp. 336-342 (2002)
[Non-patent Document 3] Luminacoids Research. vol. 22, issue 1, pp. 29-33 (2018)

DISCLOSURE OF THE INVENTION

Object of the Invention

In view of such circumstances, an object of the present invention is to provide a saccharide composition suitable for a cyclic-tetrasaccharide-containing starch syrup, wherein, even when the composition is prepared as an aqueous carbohydrate solution with relatively high concentration (starch syrup), the composition has sufficiently low viscosity and water activity, shows sufficiently low coloration, has a low calorie content, and is unlikely to cause precipitation of crystals of saccharides during storage, and to provide use of the composition and a production method for the composition.

Means to Attain the Object

In methods of producing a cyclic-tetrasaccharide-containing saccharide composition such as those described in the above Patent Document 1, α-isomaltosylglucosaccharide-forming enzyme and α-isomaltosyltransferase are allowed to act on a partial starch hydrolyzate. These methods usually produce not only a cyclic tetrasaccharide, but also a cyclic tetrasaccharide having a branched structure in which one or more glucose molecules are linked to a cyclic tetrasaccharide (hereinafter referred to as "branched cyclic tetrasaccharide"). In view of this, in the study of means for solving the problems to be solved by the present invention, the present inventors attempted to maximize the total content of the cyclic tetrasaccharide and the branched cyclic tetrasaccharide in the saccharide composition obtained by the enzyme reaction, in order to secure the low calorie property, which is one of the characteristics unique to cyclic tetrasaccharides. After setting this as the minimum requirement, means for solving the other problems were intensively studied. The present inventors considered that this requirement can be most preferably satisfied by the production methods described in Patent Document 1 and the like, that is, the methods in which the combination of α-isomaltosylglucosaccharide-forming enzyme and α-isomaltosyltransferase is allowed to act on a partial starch hydrolyzate, to produce a cyclic tetrasaccharide. However, even by taking advantage of the knowledge and know-how accumulated by the present applicant through many years of experience in production of cyclic tetrasaccharides and other carbohydrates, saccharide compositions showing good handleability and low coloration while retaining a low calorie property could not be obtained. Therefore, the present inventors stood apart from the conventional common technical knowledge, and further continued an intensively study.

More specifically, in the common technical knowledge in the art before the application of the present invention, it had been believed that, in the production of a cyclic tetrasaccharide by allowing the combination of α-isomaltosylglucosaccharide-forming enzyme and α-isomaltosyltransferase to act on a partial starch hydrolyzate, debranching reaction for the substrate carbohydrate using isoamylase or the like leads to a decrease in the rate of production of the cyclic tetrasaccharide, and that the presence of a branched structure through a α-1,6-glucosidic linkage in the substrate is preferred for the production of the cyclic tetrasaccharide by such enzymes (Non-patent Document 2). Under such circumstances, saccharide compositions containing a cyclic tetrasaccharide were prepared by use of various combinations of enzymes, including use of a starch debranching enzyme in combination. Physical properties of these compositions were then widely compared and studied.

As a result, it was found that a cyclic-tetrasaccharide-containing saccharide composition having the following characteristics (1) to (3) has all of the properties described above required for a starch syrup.

(1) The saccharide composition comprises, in addition to the cyclic tetrasaccharide, a branched cyclic tetrasaccharide comprising one or more glucose molecules linked to the cyclic tetrasaccharide, wherein the content of the cyclic tetrasaccharide with respect to the total solid content of the saccharide composition obtained by allowing glucoamylase and α-glucosidase to act on the above saccharide composition is 38% by mass or higher, on a dry solid basis;

(2) the ratio of α-1,4-linked glucose in the total glucose residues constituting the saccharide composition in methylation analysis is over 9% and 15% or lower; and (3) the ratio of α-1,4,6-linked glucose in the total glucose residues constituting the saccharide composition in methylation analysis is less than 6%.

As described later in detail in Experiments and Examples, it was found that a saccharide composition having a sufficiently low calorie content can be obtained by giving the characteristic (1), that good handleability and low coloration can both be achieved by giving the characteristics (2) and (3), and that a saccharide composition satisfying these requirements (1) to (3) is a remarkable saccharide composition which shows sufficiently low water activity when it is prepared as an aqueous solution, and which is unlikely to cause precipitation of crystals during storage even when it is prepared as a highly concentrated aqueous solution.

The saccharide composition containing a cyclic tetrasaccharide and a branched cyclic tetrasaccharide, having the characteristics described above was obtained for the first time by the combined use of a starch debranching enzyme in the reaction for production of a cyclic tetrasaccharide using α-isomaltosylglucosaccharide-forming enzyme and α-isomaltosyltransferase, and hence can be said to be a truly novel saccharide composition that could never be obtained based on the conventional common technical knowledge.

Further, the present inventors confirmed that the above-described saccharide composition is not only applicable as a starch syrup for foods and food materials, but also useful for a variety of uses such as cosmetics and quasi-drugs.

More specifically, the present invention solves the problems by providing a cyclic-tetrasaccharide-containing saccharide composition having the following characteristics (1) to (3):

(1) the saccharide composition comprises, in addition to the cyclic tetrasaccharide, a branched cyclic tetrasaccharide comprising one or more glucose molecules linked to the cyclic tetrasaccharide, wherein the content of the cyclic tetrasaccharide with respect to the total solid content of the saccharide composition obtained by allowing glucoamylase and α-glucosidase to act on the above saccharide composition is 38% by mass or higher, on a dry solid basis;

(2) the ratio of α-1,4-linked glucose in the total glucose residues constituting the saccharide composition in methylation analysis is over 9% and 15% or lower; and (3) the ratio of α-1,4,6-linked glucose in the total glucose residues constituting the saccharide composition in methylation analysis is less than 6%.

Further, the present invention solves the problems by providing a composition containing a saccharide composition having the above characteristics.

As described above, the saccharide composition containing a cyclic tetrasaccharide and a branched cyclic tetrasaccharide, having the characteristics (1) to (3) was obtained for the first time by the combined use of a starch debranching enzyme in the reaction for production of a cyclic tetrasaccharide using α-isomaltosylglucosaccharide-forming enzyme and α-isomaltosyltransferase. Accordingly, the present invention solves the problems by providing a method of producing the saccharide composition of the present invention, the method comprising the steps of: allowing α-isomaltosylglucosaccharide-forming enzyme and α-isomaltosyltransferase to act on a partial starch hydrolyzate, to produce the cyclic tetrasaccharide (Step 1); and purifying and collecting the resulting enzyme reaction product containing the cyclic tetrasaccharide (Step 2); wherein a starch debranching enzyme is also allowed to act in Step 1.

Effect of the Invention

The present invention enables production of, for example, a cyclic-tetrasaccharide-containing saccharide composition wherein, even when the composition is prepared as an aqueous carbohydrate solution with relatively high concentration (starch syrup) having a solid concentration of about 70% by mass or higher, the composition shows good handleability, is free of contamination with microorganisms, has a sufficiently low calorie content, shows sufficiently low coloration, and is unlikely to cause precipitation of crystals, which is advantageous. Further, by the production method of the present invention, a saccharide composition according to the present invention can be simply produced at low cost, which is advantageous. Since, as described above, the thus obtained saccharide composition according to the present invention has various properties generally required for starch syrup products, the composition is widely applicable to a variety of uses such as foods, which is advantageous.

MODE FOR CARRYING OUT THE INVENTION

1. Definition of Terms

The following terms in the present description have the meanings described below.

1.1 Cyclic Tetrasaccharide

When the term "cyclic tetrasaccharide" is simply used in the present description, it means a cyclic glucotetrasaccharide in which four glucose molecules are linked to each other through α-1,6 linkages and α-1,3-linkages, that is, the cyclic tetrasaccharide represented by cyclo{→6)-α-D-glucopyranosyl-(1→3)-α-D-glucopyranosyl-(1→6)-α-D-glucopyranosyl-(1→3)-α-D-glucopyranosyl-(1→}.

1.2 Branched Cyclic Tetrasaccharide

When the term "branched cyclic tetrasaccharide" is simply used in the present description, it means, unless otherwise specified, a carbohydrate having a branched structure comprising one or more glucose molecules linked to a cyclic tetrasaccharide through a glucosidic linkage(s). Specific examples of the branched cyclic tetrasaccharide include carbohydrates in which one glucose is linked to a cyclic tetrasaccharide through an α-1,4 glucosidic linkage; and carbohydrates in which one isomaltose is linked to a cyclic tetrasaccharide through an α-1,3 glucosidic linkage.

1.3 Total Cyclic Tetrasaccharide Content

When the term "total cyclic tetrasaccharide content" is used in the present description, it means the content, on a dry solid basis, of cyclic tetrasaccharide (% by mass) with respect to the total solid content of a saccharide composition obtained by allowing glucoamylase and α-glucosidase to act on a saccharide composition containing a cyclic tetrasaccharide and a branched cyclic tetrasaccharide. The total cyclic tetrasaccharide content may be used as an index of the level of the energy value of the saccharide composition since it reflects the amount of cyclic tetrasaccharide produced by digestion of the saccharide composition containing a cyclic tetrasaccharide and a branched cyclic tetrasaccharide, in a living body.

1.4. Coexisting Carbohydrate

When the term "coexisting carbohydrate" is simply used in the present description, it means all carbohydrates other than cyclic tetrasaccharides and branched cyclic tetrasaccharides contained in a saccharide composition. Examples of the coexisting carbohydrate include glucose; maltose; isomaltose; glucodisaccharides having other linkage modes; maltotriose; isomaltotnose; panose; glucotrisaccharides having other linkage modes; and glucooligosaccharides and glucans with a degree of polymerization of 4 or higher having various linkage modes, other than cyclic tetrasaccharides and branched cyclic tetrasaccharides.

1.5 α-1,4-Linked Glucose, α-1,4,6-Linked Glucose, Etc., and Ratios Thereof

The term "α-1,4-linked glucose" in present description means a glucose residue whose hydroxy groups at the 1-position and 4-position are linked to other glucose residues through α-glucosidic linkages, as detected by a methylation analysis commonly used for determining the linkage modes of the individual glucose residues constituting a glucan. Similarly, when the hydroxy groups at the 1-position, 4-position, and 6-position of a glucose residue are linked to other glucose residues through α-glucosidic linkages, the glucose residue is referred to as "α-1,4,6-linked glucose". When a glucose residue is linked to another glucose residue through the hydroxy group at another position, the number indicating the position of the hydroxy group involved in the linkage is similarly used for the name of the glucose residue (the positions of the hydroxy groups involved in the linkages, and the combination thereof, may be referred to as "linkage mode" in present description). The ratio of the glucose residues having each linkage mode (such as α-1,4-linked glucose or α-1,4,6-linked glucose) in the total glucose residues constituting the saccharide composition (which may be hereinafter referred to as the "content" of the glucose residues having each linkage mode) can be determined by the methylation analysis described above. It should be noted that the glucose residue in which only the hydroxy group at the 1-position is linked to another glucose residue, that is, the glucose residue at the non-reducing end, is not referred to as "α-1-linked glucose", but is simply referred to as "non-reducing-end glucose", in the present invention. The principle and the method of the methylation analysis are described in detail in Ciucanu et al. (Carbohydrate Research. vol. 131, issue 2, pp. 209-217 (1984)).

1.6 α-Isomaltosylglucosaccharide-Forming Enzyme

The term "α-isomaltosylglucosaccharide-forming enzyme" in present description means an enzyme that produces a carbohydrate with a degree of glucose polymerization of 3 or higher having α-1,6-glucosidic linkage as the linkage mode of the non-reducing-end residue and α-1,4-glucosidic linkage as the linkage mode of the residues other than the non-reducing-end residue, by α-glucosyl transfer from a carbohydrate with a degree of glucose polymerization of 2 or higher having α-1,4-glucosidic linkage as the linkage mode of the non-reducing-end residue, without substantially increasing the reducing power. The enzyme activity of α-isomaltosylglucosaccharide-forming enzyme is measured by performing reaction using maltotriose as a substrate, and then quantifying maltose produced by the reaction of transferring the non-reducing-end glucose from the maltotriose to another saccharide. One unit of the enzyme activity is defined as the amount of enzyme that produces 1 μmol of maltose from maltotriose in 1 minute.

1.7 α-Isomaltosyltransferase

The term "α-isomaltosyltransferase" in present description means an enzyme that produces a cyclic tetrasaccharide from a carbohydrate with a degree of glucose polymerization of 3 or higher having α-1,6-glucosidic linkage as the linkage mode of the non-reducing-end residue and α-1,4-glucosidic linkage as the linkage mode of the residues other than the non-reducing-end residue, by a reaction including α-isomaltosyl transfer. The enzyme activity of α-isomaltosyltransferase is measured by performing reaction using panose as a substrate, and then quantifying glucose produced by the reaction of transferring isomaltose from the panose to another saccharide. One unit of the enzyme activity is defined as the amount of enzyme that produces 1 μmol of glucose from panose in 1 minute.

1.8 Cyclic-Tetrasaccharide-Forming Enzyme and Enzyme Activity Unit Thereof

When the term "cyclic-tetrasaccharide-forming enzyme" is simply used in the present description, it means an enzyme composition containing α-isomaltosylglucosaccharide-forming enzyme and α-isomaltosyltransferase, but not substantially containing other enzymes. In present description, one unit of the enzyme activity of the cyclic-tetrasaccharide-forming enzyme is defined as the amount of enzyme that produces a total of 1 μmol of cyclic tetrasaccharide and branched cyclic tetrasaccharide from soluble dextrin in 1 minute, on a cyclic-tetrasaccharide basis.

1.9 Enzyme Activity Unit of Isoamylase

In present description, the enzyme activity of isoamylase is defined as follows. First, 0.5 mL of an appropriately diluted enzyme solution is added to 3 mL of an aqueous substrate solution containing 0.83% (w/v) Lintner soluble waxy corn starch and 0.1 M acetate buffer (pH 3.5). While the substrate solution is kept at 40° C., 0.5 mL of the substrate solution is sampled both after 30 seconds of the reaction and after 30 minutes 30 seconds of the reaction. The sampling is immediately followed by addition of 15 mL of 0.02 N sulfuric acid solution to each sample to stop the reaction, to provide a control solution and a reaction solution, respectively. To each of the control solution and the reaction solution obtained, 0.5 mL of 0.01 N iodine solution is added, and coloring is allowed to proceed at 25° C. for 15 minutes, followed by measurement of the absorbance at a wavelength of 610 nm using an absorptiometer, to calculate the amylolytic activity according to the following Formula [1]. One unit of isoamylase activity is defined as the amount of enzyme that increases the absorbance at a wavelength of 610 nm by 0.004 under such measurement conditions.

Formula [1]:

$$\text{Activity (units/mL)} = \{(A^{Reaction\ solution\ at\ 610\ nm} - A^{Control\ solution\ at\ 610\ nm})/0.04)\} \times \text{Dilution factor} \qquad \text{[Equation 1]}$$

1.10 Enzyme Activity Unit of Pullulanase

In present description, the enzyme activity of pullulanase is defined as follows. First, an aqueous solution of 1.25% (w/v) pullulan (manufactured by Hayashibara Co., Ltd., Okayama. Japan; for measurement of the pullulanase activity) is provided as a substrate solution. In a test tube, 4 mL of the substrate solution and 0.5 mL of 0.1 M acetate buffer (pH 5.0) are placed, and the resulting mixture is preheated at 30° C. To the test tube, 0.5 mL of an enzyme solution appropriately diluted using 0.01 M acetate buffer (pH 6.0) is added. While the substrate solution is kept at 30° C., 0.5 mL of the substrate solution is sampled both after 30 seconds of the reaction and after 30 minutes 30 seconds of the reaction. The sampling is immediately followed by injection of each sample into 2 mL of Somogyi copper solution to stop the reaction, to provide a "control solution" and a "reaction solution", respectively. The control solution and the reaction solution obtained are subjected to the Somogyi-Nelson method, and the absorbance of each sample at a wavelength of 520 nm is measured using an absorptiometer, to measure the amount of reducing sugar produced, followed by calculation of the pullulan-degrading activity according to the following Formula [2]. One unit of pullulanase activity is defined as the amount of enzyme that releases reducing sugar corresponding to 1 μmol of maltotriose in 1 minute under such measurement conditions.

Formula [2]:

$$\text{Activity (units/mL)} = \{(A^{Reaction\ solution\ at\ 520\ nm} - A^{Control\ solution\ at\ 520\ nm})/A^{Standard\ solution\ at\ 520\ nm}\} \times 100 \times 5/0.5 \times 1/180 \times 1/30 \times \text{Dilution factor} \qquad \text{[Equation 2]}$$

D-glucose (100 μg/mL) was used as the standard solution.

1.11 Enzyme Activity of Cyclomaltodextrin Glucanotransferase

In present description, the enzyme activity of cyclomaltodextrin glucanotransferase (hereinafter referred to as "CGTase") is defined as follows. First, 0.2 mL of an appropriately diluted enzyme solution is added to 5 mL of an aqueous substrate solution containing 0.3% (w/v) soluble starch, 20 mM acetate buffer (pH 5.5), and 1 mM calcium chloride. While the substrate solution is kept at 40° C., 0.5 mL of the substrate solution is sampled both after 0 minute of the reaction and after 10 minutes of the reaction. The sampling is immediately followed by addition of each sample to 15 mL of 0.02 N sulfuric acid solution to stop the reaction. Thereafter, 0.2 mL of 0.1 N iodine solution is added to each sulfuric acid solution to allow coloring to proceed for 20 minutes, and then the absorbance of each sample at a wavelength of 660 nm is measured using an absorptiometer, to calculate the amylolytic activity according to the following Formula [3]. One unit of CGTase activity is defined as the amount of enzyme that causes complete disappearance of iodine coloration for 15 mg of starch in the solution under such measurement conditions.

Formula [3]:

$$\text{Activity (units/mL)} = \{(A^{0\ minute\ of\ reaction\ at\ 660\ nm} - A^{10\ minutes\ of\ reaction\ at\ 660\ nm})/A^{0\ minute\ of\ reaction\ at\ 660\ nm}\} \times 1/0.2 \times \text{Dilution factor} \qquad \text{[Equation 3]}$$

1.12 Reducing Power

The term "reducing power" in present description means the percentage (%) of the amount of reducing sugar with respect to the total amount of saccharides in a saccharide composition, which percentage can be calculated using D-glucose as a standard substance, by determining the amount of reducing sugar and the total amount of saccharides in the saccharide composition by the Somogyi-Nelson method and the anthrone-sulfuric acid method, which are commonly used in the art, and then performing calculation according to the following Formula [4].

Formula [4]:

$$\text{Reducing power} = \text{Amount of reducing sugar/Total amount of saccharides} \times 100 \qquad \text{[Equation 4]}$$

The saccharide composition of the present invention, the use thereof, and the production method thereof are described below more concretely.

2. Saccharide Composition of Present Invention

The saccharide composition of the present invention has the following characteristics (1) to (3):

(1) the saccharide composition comprises, in addition to the cyclic tetrasaccharide, a branched cyclic tetrasaccharide comprising one or more glucose molecules linked to the cyclic tetrasaccharide, wherein the content of the cyclic tetrasaccharide with respect to the total solid content of the saccharide composition obtained by allowing glucoamylase and α-glucosidase to act on the above saccharide composition is 38% by mass or higher, on a dry solid basis;

(2) the ratio of α-1,4-linked glucose in the total glucose residues constituting the saccharide composition in methylation analysis is over 9% and 15% or lower; and (3) the ratio of α-1,4,6-linked glucose in the total glucose residues constituting the saccharide composition in methylation analysis is less than 6%.

The saccharide composition of the present invention is a saccharide composition containing the cyclic tetrasaccharide, the branched cyclic tetrasaccharide, and other coexisting carbohydrates. As described in Patent Document 2, cyclic tetrasaccharides and branched cyclic tetrasaccharides themselves do not have the reducing power, show no coloration, and are unlikely to become energy sources. On the other hand, other coexisting carbohydrates usually cause coloration due to their reducing powers, and may become energy sources. Thus, the characteristic (1) described above is directly related to maximization of the total amount of carbohydrates having a cyclic tetrasaccharide structure in the saccharide composition, and is required for securing the low calorie property of the saccharide composition. In cases where the total cyclic tetrasaccharide content is less than 38% by mass, the ratio of coexisting carbohydrates, which may cause coloration and may become energy sources, increases, so that the low calorie and the low coloration as the characteristics of the saccharide composition according to the present invention cannot be easily realized.

The characteristics (2) and (3) described above characterize the saccharide composition of the present invention on the basis of the linkage modes of the glucose residues constituting the composition. Achievement of both sufficiently low viscosity and low coloration is possible even as a highly concentrated aqueous solution in the case where the ratio of α-1,4-linked glucose residues is over 9%, preferably 9.2% or higher, more preferably 9.5% or higher, still more preferably 10% or higher regarding the lower limit of the range, and 15% or lower, preferably 14.5% or lower, more preferably 14% or lower regarding the upper limit of the range, and where the ratio of α-1,4,6-linked glucose is less than 6%, in the total glucose residues in methylation analysis. In addition, the saccharide composition of the present invention having the above characteristics shows sufficiently low water activity when it is in the form of an aqueous solution having a solid concentration similar to that of an ordinary starch syrup.

A more preferred specific example of the saccharide composition of the present invention is a saccharide composition having not only the characteristics (1) to (3) described above, but also the following characteristic:

(4) the content of cyclic tetrasaccharide with respect to the total solid content is 25% by mass or higher, on a dry solid basis.

The characteristic (4) defines the lower limit value of the content of cyclic tetrasaccharide, whose energy conversion factor, which is a factor for calculation of the energy value of a food, is 0 kcal/g (as shown by the reference test described later). By this, a saccharide composition of the present invention whose calorie is low as a whole can be provided. The content of cyclic tetrasaccharide with respect to the total solid content is more preferably 30% by mass or higher, on a dry solid basis.

Another more preferred specific example of the saccharide composition of the present invention is a saccharide composition of the present invention further having the following characteristics (5) the saccharide composition comprises carbohydrate with a degree of polymerization of 1 or 2 at a total content of 16% by mass or lower, on a dry solid basis with respect to the total solid content; and (6) the saccharide composition comprises carbohydrate with a degree of polymerization of 4 to 13 other than cyclic tetrasaccharides and branched cyclic tetrasaccharides comprising one or two linked glucose molecules, at a total content of over 37% by mass, on a dry solid basis with respect to the total solid content. The characteristic (5) defines the upper limit value of the content of saccharides with a degree of polymerization of 1 or 2, which may become energy sources and may adversely affect coloration. By this, a saccharide composition of the present invention whose coloration property is not problematic as a whole, and which has a lower calorie content, can be provided. The content is more preferably 15% by mass or lower. The characteristic (6) is an index uniquely discovered by the present inventors, and the index is related to more remarkable production of the low calorie property and the low coloration. As far as the present applicant knows, this is a characteristic that could have never been achieved by simple combination of conventional techniques for production of a cyclic-tetrasaccharide-containing starch syrup. In the characteristic (6), branched cyclic tetrasaccharides comprising three or more glucose molecules linked to the cyclic tetrasaccharide are not excluded from the carbohydrate with a degree of polymerization of 4 to 13. This is because separation of branched cyclic tetrasaccharides comprising three or more glucose molecules linked to the cyclic tetrasaccharide from other carbohydrates with the same degree of polymerization is generally difficult, so that their extraction and quantification are difficult, and because, although branched cyclic tetrasaccharides comprising three or more glucose molecules linked to the cyclic tetrasaccharide are produced also in the production method according to the present invention, their yield is very low.

When the saccharide composition of the present invention characterized as described above is prepared as an aqueous solution at a solid concentration of 73% by mass, it has a viscosity of usually 35 Pa·s or lower, preferably 30 Pa·s or lower, more preferably 27 Pa·s or lower, under an environment at 15° C. Such a low level of viscosity could not be achieved together with low coloration by conventional aqueous solutions of cyclic-tetrasaccharide-containing saccharide compositions, and it secures the property that enables achievement of favorable handleability during the process of removal from a container and mixing with other materials to obtain the final product, even in a working environment at relatively low temperature, while retaining low coloration. Further, when the saccharide composition of the present invention is prepared as an aqueous solution at the same concentration, it shows a water activity of usually less than 0.88, preferably less than 0.87, more preferably less than 0.86. This sufficiently reaches the level usually required for suppressing contamination in food production.

Another useful characteristic of the saccharide composition of the present invention is that the composition shows a dietary fiber property. In the saccharide composition of the present invention, the water-soluble dietary fiber content as determined by high-performance liquid chromatography (enzyme-HPLC method) is usually 40% by mass or higher, preferably 50% by mass or higher, more preferably 60% by mass or higher. The saccharide composition of the present invention can also be characterized by its reducing power. The reducing power is usually 7.5% to 17%, preferably 8.0% to 15%.

The saccharide composition of the present invention described above may also be provided as a reduced product of the saccharide composition by carrying out hydrogenation according to a conventional method.

3. Composition Containing Saccharide Composition of Present Invention

As described above, the saccharide composition of the present invention or the reduced product thereof has sufficiently low viscosity and water activity, shows sufficiently low coloration, has a low calorie content, and is unlikely to cause precipitation of crystals when it is prepared as an aqueous solution. Therefore, the composition can be advantageously used as a cyclic-tetrasaccharide-containing starch syrup by preparation into a highly concentrated aqueous solution; or as it is; or as a food; or as a powder base material, a binder, an excipient, or the like to be used for a cosmetic, a quasi-drug, a pharmaceutical, a livestock feed, a fish feed, a fertilizer, or the like; or as an appropriate combination with another material to provide a food or beverage, a food or beverage material, a cosmetic material, a quasi-drug material, a pharmaceutical material, a livestock-feed material, a fish-feed material, a fertilizer material, or the like. The present invention also provides such compositions containing the saccharide composition of the present invention and other materials.

In cases where the saccharide composition of the present invention or the reduced product thereof is prepared into an aqueous solution to be used as a cyclic-tetrasaccharide-containing starch syrup or a reduced starch syrup of a cyclic-tetrasaccharide-containing saccharide composition, its solid concentration is usually 70% by mass or higher, preferably 71% by mass or higher, more preferably 73% by mass or higher. Specific examples of foods and beverages in which the composition in the form of a cyclic-tetrasaccharide-containing starch syrup or a reduced starch syrup of a cyclic-tetrasaccharide-containing saccharide composition (hereinafter referred to as "cyclic-tetrasaccharide-containing starch syrup of the present invention") may be added or included include alcoholic beverages such as synthetic sake, fermented liquor, sake, fruit liquor, low-malt beer, beer, and liqueur; beverages such as carbonated beverages, milk beverages, smoothie, vegetable juices, jelly beverages, sports drinks, vinegar beverages, soymilk beverages, iron-containing beverages, lactic acid bacteria beverages, green tea, black tea, cocoa, coffee, and non-alcoholic drinks; staple foods such as cooked rice, rice gruel, rice cake, tteokbokki, and bread; noodles such as udon (thick noodle made from wheat flour), soba (buckwheat noodle), somen (thin noodle made from wheat flour), hiyamugi (thin udon noodle served cold), and ramen; pastas such as spaghetti, lasagna, macaroni, and penne; processed wheat flour products such as spring roll skin and dumpling (gyoza) skin; soups such as miso soup, tom yam kung, clam chowder, and seolleongtang; dairy products such as yogurt, cheese, and powdered milk; meat products such as sausage and ham; fish meat products such as kamaboko (steamed fish paste), chikuwa (tube-shaped fish paste), hampen (square-shaped fish paste), and fish meat sausage; processed marine products such as canned seafood, himono (dried seafood), shiokara (salted fish guts), and Matsumae pickles; cooked foods such as tempura, deep-fried food, hamburg steak, takoyaki (octopus dumpling), shumai (steamed meat dumpling), croquette, nursing food, and liquid food, and frozen foods prepared by freezing these cooked foods; confectionery such as soft candy, hard candy, gummy candy, jelly, cookie, soft cookie, senbei (rice cracker), arare (rice-cake cube), okoshi (millet-and-rice cake), alpha rice, gyuhi (starch paste), rice cakes, warabimochi (bracken-starch dumpling), manju (bun with a bean-paste filling), uiro (sweet rice jelly), "an" (sweet red-bean pastes), yokan (sweet jelly of azuki beans), mizu-yokan (soft yokan), kingyoku (a kind of yokan), jelly, pectin jelly, mousse, bavarois, castella (Japanese sponge cake), biscuit, cracker, pie, pudding, butter cream, custard cream, fresh cream, cream puff, waffle, sponge cake, pancake, muffin, donut, chocolate, ganache, chewing gum, caramel, nougat, flour paste, peanut paste, fruit paste, jam, marmalade, marshmallow, protein bar, cereal bar, and energy bar; frozen desserts such as ice cream, sherbet, and gelato; and seasonings, and cooked and processed products, such as soy sauce, powdered soy sauce, miso, powdered miso, moromi (a kind of fermented seasoning), hishio (a kind of fermented seasoning), furikake (rice seasoning), mayonnaise, dressing, vinegar, sanbaizu (a mixture of sugar, soy sauce, and vinegar), funmatsu-sushizu (powdered vinegar for sushi), chuka-no-moto (an instant mix for Chinese dish), tentsuyu (dipping sauce for tempura), mentsuyu (sauce for Japanese noodles), sauce, tomato sauce, ketchup, yakiniku-no-tare (sauce for Japanese grilled meat), yakitori-no-tare (sauce for Japanese grilled chicken), kabayaki-no-tare (broiling sauce), karaage-ko (deep-frying powder), tempura-ko (tempura flour), batter powder, takoyaki flour, okonomiyaki flour (flour for okonomiyaki, a Japanese-style pancake), bread crumb, curry roux, instant stew mix, instant soup mix, dashi-no-moto (instant stock mix), nimono-tsuyu (sauce for boiled foods), seasoning liquid for boiled fish, seasoning liquid for fish eggs, seasoning liquid for dried seafood, mixed seasoning, mirin (sweet sake), and shin-mirin (synthetic mirin). For foods and beverages prepared by fermentation, the cyclic-tetrasaccharide starch syrup of the present invention may be added after the fermentation, or may be added before the fermentation to use the cyclic-tetrasaccharide starch syrup of the present invention as a fermentation feedstock.

Since the cyclic tetrasaccharide itself is a stable substance, and effective for moisture retention, prevention of syneresis, prevention of protein denaturation, prevention of lipid deterioration, and the like, the cyclic-tetrasaccharide-containing starch syrup of the present invention can also be advantageously used by addition to cosmetics. To such cosmetics, the cyclic-tetrasaccharide-containing starch syrup of the present invention is usually added together with one or more other components whose application to the skin is acceptable, for example, one or more appropriately selected from oils and lipids, waxes, hydrocarbons, fatty acids, esters, alcohols, surfactants, dyes, perfumes, hormones, vitamins, plant extracts, animal extracts, microbial extracts, salts, ultraviolet absorbers, photosensitive pigments, antioxidants, antiseptics/microbicides, antiperspirants/deodorants, refrigerants, chelating agents, skin-whitening agents, anti-inflammatory agents, enzymes, carbohydrates, amino acids, thickeners, and the like whose external application to the skin is acceptable. Examples of the cosmetics to which the cyclic-tetrasaccharide-containing starch syrup of the present invention is added include those in the form of a lotion, cream, milky lotion, gel, powder, paste, or block, for example, cleaning cosmetics such as soaps, cosmetic soaps, facial cleansing creams, facial cleansing foams, facial rinses, body shampoos, body rinses, shampoos, rinses, and hair washing powders; hair cosmetics such as set lotions, hair blows, stick pomades, hair creams, hair sprays, hair liquids, hair tonics, hair lotions, hair restorers, hair dyes, scalp treatments, pomades, gloss-imparting hair oils, hair oils, and combing oils; base cosmetics such as cosmetic lotions, vanishing creams, emollient creams, emollient lotions, cosmetic packs (in the form of a peel-off-type jelly, wipe-off-type jelly, wash-out-type paste, powder, or the like), cleansing creams, cold creams, hand creams, hand lotions, milky lotions, moisturizing liquids, after-shaving lotions, shaving lotions, pre-shaving lotions, after-shaving creams, after-shaving foams, pre-shaving creams, cosmetic oils, and baby oils; makeup cosmetics such as foundations (in the form of a liquid, cream or the like), talcum powders, baby powders, body powders, perfume powders, makeup bases, face powders (in the form of a cream, paste, liquid, powder, or the like), eye shadows, eye creams, mascaras, eyebrow pencils, eyelash cosmetics, cheek rouges, and cheek lotions; perfume cosmetics such as perfumes, paste perfumes, powder perfumes, eau de Cologne, perfume Cologne, and eau de toilette; suntan/sunscreen cosmetics such as suntan creams, suntan lotions, suntan oils, sunscreen creams, sunscreen lotions, and sunscreen oils; nail cosmetics such as manicures, pedicures, nail colors, nail lacquers, enamel removers, nail creams, and nail cosmetic materials; eyeliner cosmetics; lip cosmetics such as lipsticks, lip creams, paste rouges, and lip glosses; oral cosmetics such as tooth pastes and mouth washes; and bath cosmetics such as bath salts, bath oils, and bath cosmetic materials.

Since the cyclic-tetrasaccharide-containing starch syrup of the present invention itself has a low calorie content, and effectively stabilizes other components added in combination, the starch syrup can also be advantageously used as an additive, excipient, or the like for pharmaceuticals. Examples of the pharmaceuticals to which the cyclic-tetrasaccharide-containing starch syrup of the present invention may be added include antibiotic preparations such as those of penicillin, erythromycin, chloramphenicol, tetracycline, streptomycin, kanamycin sulfate, or the like; vitamin preparations such as those of thiamine, riboflavin, L-ascorbic acid, cod liver oil, carotenoid, ergosterol, tocopherol, or the like; enzyme preparations such as those of lipase, esterase, urokinase, protease, β-amylase, glucanase, lactase, or the like; extract preparations such as those of a ginseng extract, soft-shelled turtle extract, chlorella extract, aloe extract, propolis extract, or the like; hormone-containing liquids such as those of macrophage migration-inhibitory factor, colony-stimulating factor, insulin, growth hormone, prolactin, erythropoietin, follicle-stimulating hormone, or the like; and biological preparations such as a BCG vaccine, Japanese encephalitis vaccine, measles vaccine, live polio vaccine, smallpox vaccine, tetanus toxoid, habu antitoxin, and human immunoglobulin. These pharmaceuticals may be provided in the form of, for example, a liquid, paste, semi-solid, or tablet.

The saccharide composition of the present invention may be provided as an intermediate product, a premix, or the like in the form of a composition prepared by combination with other materials, depending on a purpose such as the end use. The other materials that may be used for application to foods and beverages, and to orally taken quasi-drugs and pharmaceuticals, are not limited as long as these materials are acceptable as materials to be orally ingested. Examples of such materials include non-reducing carbohydrates including sugar alcohols such as sorbitol, maltitol, isomaltitol, maltotriitol, erythritol, xylitol, lactitol, panitol, trehalose, glycosyltrehalose, selaginose, selaginooligosaccharide, α-cyclodextrin, β-cyclodextrin, and γ-cyclodextrin; water-soluble dietary fibers such as isomaltodextrin, indigestible glucan, polydextrose, dextran, inulin, and fructooligosaccharide; water-soluble polysaccharides such as gum arabic, guar gum, locust bean gum, carrageenan, pectin, hemicellulose, and pullulan; high-intensity sweeteners such as dihydrochalcone, stevioside, α-glycosyl stevioside, rebaudioside, glycyrrhizin, L-aspartyl-L-phenylalanine methyl ester, acesulfame K, thaumatin, and monellin; amino acids and proteins such as glycine, alanine, glutamic acid, glutamic acid salts, and soybean peptides; nucleic acids such as inosinic acid, inosinic acid salts, guanylic acid, and guanylic acid salts; emulsifiers such as glycerin fatty acid esters, sorbitan fatty acid esters, propylene glycol fatty acid esters, sucrose fatty acid esters, lecithin, saponin, and casein sodium; vitamins such as vitamin C and sugar derivatives thereof, niacin, pantothenic acid, folic acid, biotin, hesperidin and sugar derivatives thereof, and naringin and sugar derivatives thereof; and extracts and juices from plants including tea leaves and fruits, such as green tea, oolong tea, rooibos tea, jasmine tea, coffee, and juice. The other materials that may be used for application to cosmetics, and to quasi-drugs and pharmaceuticals for external application to the skin, are not limited as long as these materials are acceptable as materials to be subjected to external application to the skin. Examples of such materials include the other materials exemplified above for application to foods and beverages, and also include water-soluble macromolecules such as quince seed, sodium alginate, cationic cellulose, hydroxyethyl cellulose, carboxymethyl cellulose, carboxymethyl starch, propylene glycol alginate, collagen, keratin, casein, albumin, gelatin, hydroxypropyl trimethyl-ammonium chloride ether, polyvinyl alcohol, polyvinyl pyrrolidone, polyvinyl pyrrolidone-vinyl acetate copolymers, polyethylene imine, sodium polyacrylate, polyvinyl methyl ether, and carboxyvinyl polymers; skin-whitening agents such as ascorbic acid 2-glucoside, kojic acid, lactic acid, anthranilic acid, coumarin, benzotriazole, imidazoline, pyrimidine, dioxane, furan, pyrone, nicotinic acid, arbutin, baicalin, and baicalein; antioxidants such as propyl gallate, butyl gallate, octyl gallate, dodecyl gallate, nordihydroguaiaretic acid, butylhydroxyanisole, dibutylhydroxytoluene, and 4-hydroxymethyl 1-2,6-di-tert-butyiphenol; and surfactants such as anionic surfactants, cationic surfactants, zwitterionic surfactants, and nonionic surfactants.

The composition and the cyclic-tetrasaccharide-containing starch syrup containing the saccharide composition of the present invention having the above characteristics can be advantageously used as materials to be added to livestock feeds and fish feeds, such as those for livestock; poultry; pets; bees; silkworms, fish and shellfish; crustaceans such as shrimps and crabs; echinoderms such as sea urchins and sea cucumbers; and larvae, juveniles, and adults of insects; and also as materials to be added to fertilizers given to juveniles such as sprouting plants, seedlings, and transplanted fungi.

4. Method of Producing Saccharide Composition of Present Invention

The method of producing the saccharide composition of the present invention is described below. The method of producing the saccharide composition of the present invention is a method of producing a saccharide composition comprising the steps of: allowing α-isomaltosylglucosaccharide-forming enzyme and α-isomaltosyltransferase to act on a partial starch hydrolyzate, to produce a cyclic-tetrasaccharide-containing saccharide composition (Step 1); and purifying and collecting the saccharide composition obtained by Step 1 (Step 2); wherein a starch debranching enzyme is also allowed to act in Step 1.

The sources of the α-isomaltosylglucosaccharide-forming enzyme and the α-isomaltosyltransferase used in the production method of the present invention are not limited as long as the saccharide composition of the present invention can be produced therewith. Specific examples of the sources include the microorganisms belonging to the genus *Bacillus* or the genus *Arthrobacter* disclosed in Patent Document 2 and the like. The *Bacillus globisporus* C9 strain (FERM BP-7143), the *Bacillus globisporus* C11 strain (FERM BP-7144), the *Bacillus globisporus* N75 strain (FERM BP-7951), and mutant strains thereof; and the *Arthrobacter globiformis* N75 strain (FERM BP-7591) and mutant strains thereof; are especially preferred as the sources of these enzymes. The enzymes may be purified enzymes obtained by separation and purification, may be crudely purified enzymes containing those enzymes, or may be extracts or cultures obtained from source microorganisms or the like. Each of the microorganism strains and the mutant strains thereof exemplified above usually produces both enzymes also into the medium when it is cultured by a conventional method. Therefore, a concentrate of a filtrate obtained by removing bacterial cells from the culture by filtration can be used as a cyclic-tetrasaccharide-forming enzyme agent containing both enzymes, and the enzyme agent is especially preferred from the viewpoint of saving the cost and the labor required for its production. Needless to say, the enzymes used may be enzymes obtained by isolating the genes encoding the enzymes and performing genetic recombination.

As a material for producing cyclic tetrasaccharide by the above-described two kinds of enzymes, a partial starch hydrolyzate is used. The origin of the starch is not limited, and may be either above-ground starch derived from maize, wheat, rice, or the like, or underground starch of potato, sweet potato, tapioca, or the like. The partial hydrolyzate of the starch can be obtained by treating the starch with an acid, α-amylase, or the like by a conventional method. The lower the degree of the hydrolysis, the higher the yield of cyclic tetrasaccharide, which is preferred. The degree of the hydrolysis in terms of DE (dextrose equivalent), which is known as an index indicating the degree of hydrolysis, is usually 20 or lower, preferably 12 or lower, more preferably 7 or lower.

An important characteristic of the method of producing the saccharide composition of the present invention is that a starch debranching enzyme is also allowed to act in Step 1, wherein α-isomaltosylglucosaccharide-forming enzyme and α-isomaltosyltransferase are allowed to act on the above-described partial starch hydrolyzate to produce cyclic tetrasaccharide. The type and the source of the starch debranching enzyme used in the present invention are not limited as long as the saccharide composition of the present invention can be produced therewith. Examples of the starch debranching enzyme include isoamylase (EC 3.2.1.68), pullulanase (EC 3.2.1.41), oligo-1,6-glucosidase (EC 3.2.1.10), and amylo-1,6-glucosidase (EC 3.2.1.33). Among these, isoamylase produced by *Pseudomonas amyloderamosa* and pullulanase produced by a microorganism belonging to the genus *Bacillus* (*Bacillus* sp.) are especially preferred since the viscosity of the saccharide composition obtained as a result can be effectively reduced without preventing the reaction for producing the cyclic tetrasaccharide.

In Step 1, wherein cyclic tetrasaccharide is produced by the above-described enzyme actions, the yield of cyclic tetrasaccharide can be further increased by also allowing CGTase (EC 2.4.1.19) to act. Thus, CGTase may be used in combination with the above-described enzymes. The source of the CGTase is not limited, and examples of the source include *Geobacillus stearothermophilus, Paenibacillus illinoisensis, Paenibacillus pabuli*, and *Paenibacillus amylolyticus*. Among these, *Geobacillus stearothermophilus* is especially useful since it produces a CGTase that effectively increases the yield of cyclic tetrasaccharide.

In the method of producing the saccharide composition of the present invention, use of exo-type amylase is more preferably avoided throughout the entire process since, in this case, low viscosity and low coloration can be achieved when the saccharide composition is used as a starch syrup. In cases where such an exo-type amylase is allowed to act during the step of producing the cyclic tetrasaccharide or after this step, the content of reducing monosaccharides, disaccharides, and the like increases, resulting in difficulty in realization of the low coloration, so that the object of the present invention cannot be easily achieved. Examples of exo-type amylases whose use is preferably avoided in the method of producing the saccharide composition of the present invention include those having actions of producing monosaccharides or disaccharides, such as glucoamylase (EC 3.2.1.3), α-glucosidase (EC 3.2.1.20), and β-amylase (EC 3.2.1.2). In enzymatic production of a common starch syrup, an endo-type amylase such as α-amylase is allowed to act for finishing in the final stage of the enzyme reaction in some cases. This is carried out for the purpose of reducing the molecular weight of the glucan macromolecules that are remaining in a small amount upon the completion of the enzyme reaction for producing the saccharide composition to be prepared into the starch syrup, to thereby enhance the efficiency of the subsequent purification step. This operation usually does not substantially change the saccharide composition. Also in the method of producing the saccharide composition of the present invention, an endo-type amylase may be allowed to act for finishing, and such an endo-type amylase is more preferably a liquefying amylase. Further, when necessary, an exo-type amylase having an action that produces maltooligosaccharides with a degree of polymerization of 3 or higher, more preferably an exo-type amylase having an action that produces maltooligosaccharides with a degree of polymerization of 4 or higher, may be used in combination since they hardly produce monosaccharides and disaccharides.

Conditions for allowing the actions of the enzymes in Step 1 for producing the cyclic tetrasaccharide, such as the concentration of the raw material, the reaction time, the reaction temperature, and the reaction pH, may be appropriately selected depending on the purpose and situations such as the value of the total cyclic tetrasaccharide content to be achieved, and the types and the origins of the enzymes used. The reaction temperature is usually 40° C. to 60° C., preferably 45° C. to 55° C. The reaction pH is usually over 4.5 and less than 7.0, preferably 5.0 to 6.7, more preferably 5.5 to 6.3. In cases where the enzyme reaction is expected to be completed in 48 hours, the concentration of the raw-material partial starch hydrolyzate in terms of the solid concentration is usually preferably 1% by mass or higher regarding the lower limit, and is usually 40% or lower, preferably 35% by mass or lower, more preferably 33% by mass or lower regarding the upper limit. Regarding the amounts of the enzymes to be allowed to act, in cases where a cyclic-tetrasaccharide-forming enzyme is used as the α-isomaltosylglucosaccharide-forming enzyme and the α-isomaltosyltransferase, its amount is within the range of usually 0.2 unit to 5 units, preferably 0.7 unit to 4 units, more preferably 1 unit to 3 units, still more preferably 1.2 units to 2.5 units, per 1 g of the raw-material solid. In cases where isoamylase is used as the starch debranching enzyme, its amount is within the range of usually 100 units to 2000 units, preferably 200 units to 1000 units, more preferably 400 units to 600 units, per 1 g of the raw-material solid. In cases where pullulanase is used, its amount is within the range of usually 0.5 unit to 10 units, preferably 1 unit to 8 units, more preferably 2 units to 6 units, per 1 g of the raw-material solid. In cases where CGTase is used, its amount is within the range of usually 0.1 unit to 5 units, preferably 0.2 unit to 3 units, more preferably 0.4 unit to 2 units, per 1 g of the raw-material solid. In cases where the total reaction time is set to a time other than 48 hours, the amounts of the enzymes to be allowed to act may be appropriately adjusted depending on the length of the total reaction time. The timing of the addition of each enzyme is not limited. All enzymes used may be added at the same time, or the enzymes may be sequentially added. Depending on conditions such as the concentration of the raw material included, the enzymes are preferably sequentially added so as to increase the total cyclic tetrasaccharide content without increasing coloration of the resulting saccharide composition. In this case, the cyclic-tetrasaccharide-forming enzyme, the CGTase, and the starch debranching enzyme are preferably added in this order. The timing of the addition of the starch debranching enzyme is usually earlier than the time point when 1/2 of the total reaction time passes, preferably earlier than the time point when 1/5 of the total reaction time passes. Depending on conditions, for example, when the solid concentration of the raw material is 30% by mass or higher, the starch debranching enzyme is not recommended to be added after the production of the cyclic tetrasaccharide has reached the plateau since this does not sufficiently cause a decrease in the viscosity of the resulting saccharide composition under some conditions. In cases where an endo-type amylase is used for finishing of the cyclic-tetrasaccharide-forming reaction, when a reaction time of about 2 hours is assumed, the amount of the enzyme to be allowed to act is usually 1 unit to 40 units, preferably 2 units to 25 units, more preferably 4 units to 15 units, per 1 g of the raw-material solid.

The reaction solution after the completion of the reaction for producing the cyclic tetrasaccharide is then subjected to Step 2, wherein the reaction product is purified and collected. The purification may be carried out according to a conventional method in the art. Examples of the conventional method include diatomaceous earth filtration, decoloration using activated carbon, and desalting using an H-type and/or OH-type ion-exchange resin(s). The purification may be followed by adjustment of the concentration as appropriate, and then the product may be collected as a solid by spray drying, vacuum drying, freeze-drying, or the like. Alternatively, the purification may be followed by concentration for adjustment to a desired concentration, and then the product may be collected as a starch syrup. The saccharide composition of the present invention can thus be produced. In the method of producing the saccharide composition of the present invention, hydrogenation may be carried out according to a conventional method after the reaction for enzymatically producing the cyclic tetrasaccharide, but before the collection of the product, to obtain a reduced product of the saccharide composition. The method of producing the saccharide composition of the present invention described above is merely a preferred example for obtaining the saccharide composition of the present invention. As long as a saccharide composition of the present invention having the characteristics (1) to (3) can be obtained, the saccharide composition may be produced by, for example, appropriately adding a separately prepared branched cyclic tetrasaccharide and coexisting carbohydrates to a highly pure cyclic tetrasaccharide.

The present invention is described below based on Experiments and Examples. However, these are merely specific examples, and the present invention is not limited thereto.

Experiment 1: Preparation of Various Cyclic-Tetrasaccharide-Containing Starch Syrups, and Evaluation of Physical Properties Thereof

Experiment 1-1: Preparation of Various Cyclic-Tetrasaccharide-Containing Starch Syrups A total of seven kinds of cyclic-tetrasaccharide-containing saccharide compositions (starch syrups) were prepared as test samples by carrying out cyclic-tetrasaccharide-forming reaction using α-isomaltosylglucosaccharide-forming enzyme and α-isomaltosyltransferase based on the reaction system (the later-mentioned reaction system for Test Sample 1) of a conventional technique in which the value of the total cyclic tetrasaccharide content has been shown to be sufficiently higher than the contents of other carbohydrates, while employing various enzymes and changing the timings of their addition.

Experiment 1-1-1: Materials

Raw Material for Cyclic Tetrasaccharide-Forming Reaction

As a raw material for the cyclic-tetrasaccharide-forming reaction, a liquefied liquid obtained by partially hydrolyzing corn starch by a conventional method using a high-temperature liquefying enzyme was used. The solid concentration and the DE of the raw material were determined by conventional methods. As result, they were 30% by mass and DE 5, respectively.

Enzymes

A cyclic-tetrasaccharide-forming enzyme containing α-isomaltosylglucosaccharide-forming enzyme and α-isomaltosyltransferase was prepared according to the method of Experiment 3 of Patent Document 1, by culturing the *Bacillus globisporus* C9 strain (FERM BP-7143) and removing the bacterial cells from the resulting culture using an SF membrane according to a conventional method, followed by concentrating the resulting filtrate using a UF membrane. The enzyme activity was measured as follows. First, 500 μL of a liquid prepared by appropriately diluting the cyclic-tetrasaccharide-forming enzyme was mixed with 500 μL of 50 mM acetate buffer (pH 6.0) containing 2% (w/v) soluble dextrin (trade name, "PINE-DEX #100"; manufactured by Matsutani Chemical Industry Co., Ltd., Hyogo, Japan), and the resulting mixture was kept at 40° C. for 1 hour to allow the reaction to proceed, followed by stopping the reaction by boiling for 10 minutes, and then performing analysis of the total cyclic tetrasaccharide content (described later) to quantify the total cyclic tetrasaccharide produced by the reaction, to thereby determine the enzyme activity. The activity of the cyclic-tetrasaccharide-forming enzyme obtained was 492 units/mL.

As α-glucosidase, the enzyme manufactured by Amano Enzyme Inc., Aichi, Japan (trade name, "Transglucosidase L 'Amano'"; 13,000 units/mL) was used. As glucoamylase, the enzyme manufactured by Nagase ChemteX Corporation, Osaka, Japan (trade name, "Denazyme GSA/R"; 3,800 units/g) was used. As isoamylase, the enzyme manufactured by Hayashibara Co., Ltd., Okayama, Japan (derived from *Pseudomonas amyloderamosa*, 553,500 units/g) was used. As pullulanase, the enzyme manufactured by Amano Enzyme Inc., Aichi, Japan (trade name, "Pullulanase 'Amano' 3"; 3000 units/g) was used. As CGTase, the enzyme manufactured by Hayashibara Co., Ltd., Okayama, Japan (derived from *Geobacillus stearothermophilus*, 1,634 units/g) was used. As α-amylase, the enzyme manufactured by Nagase ChemteX Corporation, Osaka, Japan (trade name, "NEO-Spitase PK-6/R"; 37,500 units/g) was used.

Experiment 1-1-2: Preparation of Various Cyclic-Tetrasaccharide-Containing Starch Syrups

Test Sample 1

To the raw material (coin starch-liquefied liquid; DE 5; solid concentration, 30% by mass), 2 units of the cyclic-tetrasaccharide-forming enzyme per 1 g of the raw-material solid and 1 unit of CGTase per 1 g of the raw-material solid were added, and the resulting mixture was kept at pH 6.0 at 50° C. for 48 hours, to carry out the cyclic-tetrasaccharide-forming reaction according to the method described in Example A-9 of Patent Document 1. Thereafter, the reaction solution was kept at 95° C. for 30 minutes to stop the reaction, and then cooled to normal temperature, followed by filtration, desalting using H-type and OH-type ion-exchange resins, decoloration using activated carbon, and then concentration to a solid concentration of 73% by mass using an evaporator according to conventional methods, to obtain Test Sample 1.

Test Sample 2

The same operation as the operation for Test Sample 1 was carried out except that 500 units of isoamylase per 1 g of the raw-material solid was added at the time point when 5 hours have passed after the beginning of the cyclic-tetrasaccharide-forming reaction, to obtain Test Sample 2.

Test Sample 3

The same operation as the operation for Test Sample 1 was carried out except that 5 units of pullulanase per 1 g of the raw-material solid was added at the time point when 5 hours have passed after the beginning of the cyclic-tetrasaccharide-forming reaction, to obtain Test Sample 3.

Test Sample 4

The same operation as the operation for Test Sample 1 was carried out except that the operation of adding 5 units of α-amylase per 1 g of the raw-material solid after the completion of the cyclic-tetrasaccharide-forming reaction, keeping the resulting mixture at pH 6.0 at 50° C. for 20 hours, and then keeping the mixture at 95° C. for 30 minutes to stop the reaction was included, to obtain Test Sample 4.

Test Sample 5

The same operation as the operation for Test Sample 1 was carried out except that the operation of adding 500 units of isoamylase per 1 g of the raw-material solid after the completion of the cyclic-tetrasaccharide-forming reaction, keeping the resulting mixture at pH 6.0 at 50° C. for 20 hours, and then keeping the mixture at 95° C. for 30 minutes to stop the reaction was included, to obtain Test Sample 5.

Test Sample 6

The same operation as the operation for Test Sample 1 was carried out except that the operation of adding 5 units of α-amylase per 1 g of the raw-material solid, 1 unit of glucoamylase per 1 g of the raw-material solid, and 500 units of isoamylase per 1 g of the raw-material solid after the completion of the cyclic-tetrasaccharide-forming reaction, keeping the resulting mixture at pH 6.0 at 50° C. for 20 hours, and then keeping the mixture at 95° C. for 30 minutes to stop the reaction was included, to obtain Test Sample 6.

Test Sample 7

The same operation as the operation for Test Sample 1 was carried out except that the operation of adding 5 units of α-amylase per 1 g of the raw-material solid, 1 unit of glucoamylase per 1 g of the raw-material solid, and 5 units of pullulanase per 1 g of the raw-material solid after the completion of the cyclic-tetrasaccharide-forming reaction, keeping the resulting mixture at pH 6.0 at 50° C. for 20 hours, and then keeping the mixture at 95° C. for 30 minutes to stop the reaction was included, to obtain Test Sample 7.

Test Sample 8

The same operation as the operation for Test Sample 1 was carried out except that 2.5 units of the cyclic-tetrasaccharide-forming enzyme per 1 g of the raw-material solid and 0.5 unit of CGTase per 1 g of the raw-material solid were added upon the cyclic-tetrasaccharide-forming reaction, that 400 units of isoamylase per 1 g of the raw-material solid was added at the time point when 5 hours have passed after the beginning of the cyclic-tetrasaccharide-forming reaction, followed by keeping the resulting mixture until 56 hours have passed after the beginning of the cyclic-tetrasaccharide-forming reaction, and that 5 units of α-amylase per 1 g of the raw-material solid was added after the completion of the cyclic-tetrasaccharide-forming reaction, followed by allowing the reaction to proceed at 80° C. for 2 hours, to obtain Test Sample 8.

Experiment 1-2: Analysis

Saccharide Composition Analysis

The contents (% by mass) of carbohydrates such as cyclic tetrasaccharide contained in each obtained test sample, on a dry solid basis with respect to the total solid content, were determined by subjecting the test sample to high-performance liquid chromatography (hereinafter referred to as HPLC) using a commercially available high-performance liquid chromatography system (trade name, "Prominence"; manufactured by Shimadzu Corporation, Kyoto, Japan) under the following conditions, and performing calculation by the percentage method based on the chromatogram obtained. In this analysis, the content was determined for each of the following: cyclic tetrasaccharide; the total of branched cyclic tetrasaccharides containing one or two linked glucose molecules, the total of glucose, maltose, and isomaltose as carbohydrates with a degree of polymerization of 1 or 2; and "others", which is the total of all other carbohydrates.

HPLC Conditions

Column: two "MCI GEL CK04SS" (manufactured by Mitsubishi Chemical Corporation, Tokyo. Japan) columns connected in series Sample concentration: 1% by mass in terms of the solid concentration Sample injection volume: 20 μL Eluent: Ultrapure water Flow rate: 0.4 mL/minute Temperature: 80° C.

Detection: differential refractive index

Analysis of Total Cyclic Tetrasaccharide Content

The total cyclic tetrasaccharide content in each obtained test sample was determined by mixing 0.5 mL of a solution whose solid concentration was adjusted to 2% by mass, with 0.5 mL of 50 mM acetate buffer (pH 5.0) containing 400 units/mL of α-glucosidase and 10 units/mL of glucoamylase, keeping the resulting mixture at 50° C. for 24 hours to completely digest the linkages between glucose molecules other than those in cyclic tetrasaccharides, stopping the digestion reaction by boiling for 10 minutes, subjecting the resulting product to desalting and to filtration through a membrane filter by conventional methods, performing HPLC under the following conditions, and then performing the area percentage method based on the chromatogram obtained. By the enzyme reaction under these conditions, a saccharide composition containing cyclic tetrasaccharide, branched cyclic tetrasaccharide, and coexisting carbohydrate, such as the test samples, undergoes complete hydrolysis of the sugar-chain moiety excluding the cyclic tetrasaccharide, to produce glucose. As a result, after the reaction, the composition becomes a saccharide composition substantially composed only of the cyclic tetrasaccharide and the glucose.

HPLC Conditions

Column: "Shodex Sugar KS-801 (Na Type)" (manufactured by Showa Denko K. K., Tokyo, Japan)

Flow rate: 0.5 mL/minute

Temperature: 60° C.

The apparatuses and conditions not described here were the same as those in the above saccharide composition analysis (low-polymerization-degree side).

Viscosity Measurement

The viscosity of each test sample was determined by measurement using a rheometer (trade name, "MCR102", manufactured by Anton Paar Japan K. K., Tokyo, Japan) under conditions where the sample temperature and the ambient temperature were 15° C.

Water Activity Measurement

The water activity of each test sample was measured using a water activity measurement system (trade name, "AquaLab Series 4TDL", manufactured by AINX Co., Ltd., Tokyo, Japan).

Experiment 1-3: Results and Discussion

The results obtained by subjecting the Test Samples 1 to 8 obtained in Experiment 1-1 to saccharide composition analysis, total cyclic tetrasaccharide content analysis, viscosity measurement, and water activity analysis according to the methods described in Experiment 1-2 are shown in Table 1. Table 1 also shows the type and the timing of addition of each enzyme used for the preparation of Test Samples 1 to 8, wherein "+" indicates that the enzyme was added, and "−" indicates that the enzyme was not added.

TABLE 1

| | | Test sample No. | | | | | | | |
|---|---|---|---|---|---|---|---|---|---|
| | | 1 | 2 | 3 | 4 | 5 | 6 | 7 | 8 |
| Enzyme used*1 | Cyclic-tetrasaccharide-forming enzyme | + | + | + | + | + | + | + | + |
| | CGTase | + | + | + | + | + | + | + | + |
| | Isoamylase (addition at Hour 5 in the reaction) | − | + | − | − | − | − | − | + |
| | Pullulanase (addition at Hour 5 in the reaction) | − | − | + | − | − | − | − | − |
| | α-Amylase (addition after the completion of the reaction) | − | − | − | + | − | + | + | + |
| | Glucoamylase (addition after the completion of the reaction) | − | − | − | − | − | + | + | − |
| | Isoamylase (addition after the completion of the reaction) | − | − | − | − | + | + | − | − |
| | Pullulanase (addition after the completion of the reaction) | − | − | − | − | − | − | + | − |
| Total cyclic tetrasaccharide content (% by mass) | | 49.1 | 48.4 | 44.3 | 48.9 | 49.5 | 48.4 | 48.9 | 49.6 |
| Saccharide composition | Cyclic tetrasaccharide | 30.4 | 31.7 | 29.2 | 30.5 | 31.1 | 29.8 | 29.2 | 33.2 |
| (% by mass) | Branched cyclic tetrasaccharide *2 | 13.8 | 15.0 | 15.5 | 14.0 | 14.4 | 16.3 | 18.0 | 16.4 |
| | DP1 + DP2 *3 | 4.8 | 9.7 | 15.0 | 4.9 | 5.5 | 19.1 | 21.1 | 11.5 |
| | Others *4 | 51.0 | 43.6 | 40.3 | 50.6 | 49.0 | 34.8 | 31.7 | 38.9 |

TABLE 1-continued

| | Test sample No. | | | | | | | |
|---|---|---|---|---|---|---|---|---|
| | 1 | 2 | 3 | 4 | 5 | 6 | 7 | 8 |
| Viscosity (Pa · s) | 45.6 | 26.4 | 18.1 | 36.1 | 38.3 | 18.7 | 13.4 | 32.4 |
| Water activity | 0.87 | 0.86 | 0.85 | 0.87 | 0.87 | 0.84 | 0.84 | 0.86 |

*[1]"Addition at Hour 5 in the reaction" means that the enzyme was added when 5 hours have passed after the beginning of the cyclic-tetrasaccharide-forming reaction, and "addition after the completion of the reaction" means that the enzyme was added after the completion of the cyclic-tetrasaccharide-forming reaction.
*[2] "Branched cyclic tetrasaccharide" means the total content of branched cyclic tetrasaccharides containing one or two linked molecules of glucose residues.
*[3] "DP1 + DP2" means the total content of glucose, maltose, and isomaltose.
*[4] "Others" means the total content of all other saccharides.

As can be seen from Table 1, also in the cases where other enzymes listed in Table 1 were allowed to act in addition to the cyclic-tetrasaccharide-forming enzyme and CGTase (Test Samples 2 to 8), the level of the total cyclic tetrasaccharide content was equivalent to that in the case of Test Sample 1, which was obtained by a conventional method. The energy conversion factor is a factor for calculation of the energy value of a food. While glucose has an energy conversion factor of 4 kcal/g, cyclic tetrasaccharide has an energy conversion factor of 0 kcal/g (as shown in the reference test described later). Taking into account this fact together with the calculation results on the energy value in the later-described Experiment 4, Example 1, and Comparative Example 1, it is thought that a low calorie property can be sufficiently appealed as a carbohydrate material in cases where the total cyclic tetrasaccharide content is 38% by mass or higher. Moreover, the water activity was 0.88 or lower in all cases, so that the water activity was also satisfactory from the viewpoint of the value required for avoiding microbial contamination in foods. Test Sample 1, which was obtained by the conventional technique, showed a viscosity of 45.6 Pa·s. On the other hand, Test Samples 2, 3, and 8, which were obtained by a process in which the starch debranching enzyme isoamylase or pullulanase was allowed to act during the reaction for producing cyclic tetrasaccharide, showed viscosities of 26.4 Pa·s, 18.1 Pa·s, and 32.4 Pa·s, respectively. Thus, they showed remarkably lower viscosities than that of Test Sample 1, which was obtained by the conventional method.

On the other hand, Test Sample 4, which was obtained by a process in which the endo-type amylase α-amylase was allowed to act after the reaction for producing cyclic tetrasaccharide, without allowing a starch debranching enzyme to act, and Test Sample 5, which was obtained by a process in which the starch debranching enzyme isoamylase was allowed to act after the reaction rather than during the reaction, showed no significant decrease in the viscosity (viscosities: 36.1 Pa·s and 38.3 Pa·s, respectively) compared to Test Sample 1. Test Samples 6 and 7, which were obtained by a process in which glucoamylase, which is an exo-type amylase having an activity that produces monosaccharides, and α-amylase, which is an endo-type amylase, as well as the starch debranching enzyme isoamylase or pullulanase, were allowed to act after the reaction for producing cyclic tetrasaccharide, showed remarkably lower viscosities (18.7 Pa·s and 13.4 Pa·s, respectively) than that of Test Sample 1, which was used as the base. On the other hand, Test Sample 8, which was obtained by a process in which the starch debranching enzyme isoamylase was allowed to act during the reaction for producing cyclic tetrasaccharide, and in which the endo-type amylase α-amylase alone was allowed to act after the reaction, showed a viscosity of 32.4 Pa·s, which was lower than that of Test Sample 1, and also lower than the practically acceptable level, 35 Pa·s.

From the viewpoint of the measured value of the viscosity alone, Test Samples 2, 3, 6, 7, and 8 were expected to enable achievement of the object of the present invention. However, the extent to which the measured value of the viscosity reflects the actual handleability was still unclear, and coloration could not be judged based on the above results alone.

Experiment 2: Evaluation of Handleability and Coloration of Various Cyclic-Tetrasaccharide-Containing Starch Syrups Based on the results of Experiment 1, evaluation in Experiment 2 was carried out to clarify the following.
(i) Whether or not the differences in the viscosity found among the test samples in Experiment 1 affect the actual handleability.
(ii) Whether or not there are differences in the coloration among the test samples obtained in Experiment 1.

Experiment 2-1: Methods

Method of Evaluation of Handleability

Under conditions where the ambient temperature and the temperatures of all materials used were set to 15° C., 500 g of each test sample prepared in Experiment 1 was placed in a 1-L glass beaker, and 200 g of deionized water was gently added thereto, followed by mixing the sample using a metal spatula to make the whole sample homogeneous. To provide a control, a commercially available maltotetraose-containing starch syrup (trade name, "TETRUP"; manufactured by Hayashibara Co., Ltd., Okayama, Japan; maltotetraose content, 50% by mass or higher) whose solid concentration had been adjusted to 73% by mass in advance was treated under the same conditions, and then the sample was mixed using a metal spatula to make the whole sample homogeneous. The time and the force required for each test sample to become entirely homogeneous by the mixing were compared with the time and the force required for the control sample to become entirely homogeneous by the mixing, and rated on the following 3-point scale.
  "○" ("Excellent" handleability): Equivalent to the control.
  "Δ" ("Good" handleability): Somewhat more time and force were required compared to the control, but there was no problem in the handleability.
  "x" ("Poor" handleability): More time and force were clearly required compared to the control, and there was a problem in the handleability.

Method of Evaluation of Coloration

In a sealed container, 50 mM acetate buffer (pH 6.0) containing each of Test Samples 1 to 8 at 10% by mass as a solid, and also containing 1% by mass glycine, was enclosed. The container was then kept in a boiling water bath for 1 hour. To provide a control, the above-described commercially available maltotetraose-containing starch syrup was subjected to the same operation. After completion of the keeping in the boiling water bath for 1 hour, each sample was rapidly cooled, and the absorbance at 460 nm was measured by a conventional method, followed by visually comparing the degree of coloration among the samples. The absorbance of the control sample was 0.100. The result for each test sample was compared with the result for the control sample, and the coloration was rated on the following 3-point scale.

"○" ("Low" coloration): The absorbance was 1.3 times the absorbance of the control or lower, and visual difference in the coloration could be hardly found in the comparison with the control.

"Δ" ("Medium" coloration): The absorbance was over 1.3 times the absorbance of the control, but was 1.6 times the absorbance of the control or lower. Some coloration was visually found in the comparison with the control, but the coloration was judged to be within the acceptable range in ordinary food production.

"x" ("High" coloration): The absorbance was over 1.6 times the absorbance of the control. Intense coloration was visually clearly found in the comparison with the control, and the coloration was judged to be unacceptable in ordinary food production.

2-2: Results and Discussion

The results are shown in Table 2.

TABLE 2

| | Test sample No. | | | | | | | |
| --- | --- | --- | --- | --- | --- | --- | --- | --- |
| | 1 | 2 | 3 | 4 | 5 | 6 | 7 | 8 |
| Handleability | x | ○ | ○ | x | x | ○ | ○ | ○ |
| Coloration | ○ | ○ | Δ | ○ | ○ | x | x | Δ |

As shown in Table 2, Test Samples 2, 3, and 8 were rated as "○" (excellent) in terms of the handleability, which is thought to be related to the viscosity. Thus, they had no problem in the handleability. Also from the viewpoint of the coloration, they were rated as "○" (low) or "Δ" (medium), indicating that they had no problem. On the other hand, while Test Samples 6 and 7, whose viscosities were also low, were both rated as "○" (excellent) in terms of the handleability, they were unsatisfactory from the viewpoint of the coloration. Test Samples 6 and 7, which were rated as "x" (high) in terms of the coloration, contain over 16% by mass carbohydrates with a degree of polymerization of 1 or 2. It was thus thought that the problem in the coloration can be avoided by setting the content of carbohydrates with a degree of polymerization of 1 or 2 to 16% by mass or lower. Test Samples 4 and 5 were rated as "○" (excellent) in terms of the coloration, but they were rated as "x" (poor) in terms of the handleability. Based on the above results as well as the low calorie property and the low water activity confirmed in Experiment 1, Test Samples 2, 3, and 8 were thought to enable achievement of the object of the present invention.

Subsequently, Experiment 3 was carried out as follows in order to elucidate the structural characteristic by which Test Samples 2, 3, and 8 showed low viscosity and good handleability irrespective of the fact that their total cyclic tetrasaccharide contents were not remarkably different from those of other test samples.

Experiment 3: Study of Structure Involved in Handleability of Cyclic-Tetrasaccharide-Containing Starch Syrup In order to clarify the structural difference that affects the differences in the handleability among the test samples, the following analysis was carried out focusing on the content of glucose residues having each linkage mode and the content of carbohydrates with a medium degree of polymerization in each test sample.

Experiment 3-1: Methods

Methylation Analysis

According to a method described in Ciucanu et al. (Carbohydrate Research. vol. 131, issue 2, pp. 209-217 (1984)), each test sample obtained in Experiment 1 was first subjected to methylation of free hydroxy groups and complete hydrolysis, to obtain methylated glucose. The methylated glucose was reduced to prepare methylated glucitol, and hydroxy groups of the methylated glucitol obtained were acetylated to finally obtain methylated glucose acetate. The methylated glucose acetate obtained from each test sample was then subjected to gas chromatography (hereinafter referred to as "GC") using a commercially available gas chromatography system (trade name, "GC-2010 Plus"; manufactured by Shimadzu Corporation, Kyoto, Japan) under the following conditions, to determine the content (%) of glucose residues having each linkage mode in each test sample.

GC Conditions

Column: InertCap5 Capillary Column (0.25 mm (inner diameter)×30 m (length)×0.25 μm (film thickness), manufactured by GL Sciences, Inc., Tokyo, Japan)
Carrier Gas: Helium
Column Temperature: retention at 130° C. for 3 minutes, heating to 250° C. at 5° C./minute, and then retention at 250° C. for 10 minutes
Flow rate: 1.0 mL/minute
Detection: FID
Injection volume: 1 μL (split 1/50)
Analysis time: 46 minutes

Measurement of Content of Carbohydrates with a Medium Degree of Polymerization Under the same conditions as in the HPLC for the purpose of the saccharide composition analysis in Experiment 1, a maltooligosaccharide mixture with a known degree of polymerization was analyzed. The resulting chromatogram was compared with the chromatogram obtained for each test sample in Experiment 1, to measure the content of carbohydrates with a medium degree of polymerization that had not been evaluated or studied in detail in Experiment 1, that is, carbohydrates judged to correspond to a degree of polymerization of 4 to 13 (however, cyclic tetrasaccharides, and branched cyclic tetrasaccharides containing one or two glucose molecules linked to a cyclic tetrasaccharide, were excluded herein due to the properties of HPLC under the above conditions), by the area percentage method.

Measurement of Reducing Power

The reducing power was determined using D-glucose as a standard substance by measuring the amount of reducing sugar by the Somogyi-Nelson method as described below, and measuring the total amount of saccharides by the each test sample. Since the measurement of the content of carbohydrates with a medium degree of polymerization showed a certain relationship between the viscosity observed for each test sample and the content of carbohydrates corresponding to a degree of polymerization of 4 to 13, the content of carbohydrates with such a degree of polymerization is also shown in Table 3. The results on the handleability and the coloration were copied from Table 2.

TABLE 3

| | | Test sample No. | | | | | | | |
| --- | --- | --- | --- | --- | --- | --- | --- | --- | --- |
| | | 1 | 2 | 3 | 4 | 5 | 6 | 7 | 8 |
| Handleability*[1] | | x | ○ | ○ | x | x | ○ | ○ | ○ |
| Coloration*[1] | | ○ | ○ | Δ | ○ | ○ | x | x | Δ |
| Content (%) of | α-1,4 | 15.4 | 11.2 | 10.8 | 15.3 | 15.6 | 8.2 | 6.3 | 9.2 |
| glucose residues | α-1,4,6 | 6.4 | 5.0 | 4.5 | 6.3 | 5.7 | 5.2 | 5.2 | 3.9 |
| having each linkage | α-1,3 | 33.3 | 34.9 | 34.6 | 33.0 | 33.4 | 35.8 | 35.7 | 33.7 |
| mode*[2] as | α-1,6 | 29.9 | 30.8 | 28.7 | 30.1 | 29.4 | 29.6 | 27.4 | 31.5 |
| determined by | α-1,3,6 | 3.2 | 3.4 | 3.8 | 3.1 | 3.3 | 3.3 | 5.1 | 4.0 |
| methylation analysis | α-1,2 | 0.0 | 0.0 | 0.0 | 0.0 | 0.0 | 0.0 | 0.0 | 0.0 |
| | Non-reducing | 11.8 | 14.7 | 17.6 | 12.2 | 12.6 | 18.0 | 20.4 | 17.5 |
| Content (% by mass) of carbohydrates with DP4 to 13 | | 31.5 | 39.2 | 37.4 | 33.5 | 37.0 | 30.5 | 28.9 | 37.1 |
| Reducing power (%) | | 4.1 | 8.5 | 13.6 | 7.1 | 5.5 | 17.6 | 19.8 | 12.4 |

*[1]Copied from Table 2.
*[2]"α-1,4" means α-1,4-linked glucose (the same applies hereinafter). "Non-reducing" means the non-reducing-end glucose.

anthrone-sulfuric acid method, followed by substituting these into the above-described Formula [4] to perform the calculation.

Measurement by Somogyi-Nelson Method

After mixing 2 mL of Somogyi copper reagent with 1 mL of a sample diluted to within the range of a calibration curve, the resulting mixture was boiled for 10 minutes, and then cooled by flowing water. Thereafter, 2 mL of Nelson reagent was added to the cooled liquid, and then the resulting mixture was quickly mixed. The mixture was left to stand until its color changed from the yellow-green after the addition of Nelson reagent to blue, and then 5 mL of water was added thereto, followed by stirring the mixture and measuring the absorbance at a wavelength of 520 nm. Based on the measured absorbance and the calibration curve, the amount of reducing sugar was determined. The calibration curve was prepared using a D-glucose standard solution.

Measurement by Anthrone-Sulfuric Acid Method

Into 5 mL of 0.2% anthrone reagent precooled in ice water, 0.5 mL of each sample diluted to within the range of a calibration curve was gently poured, and the resulting mixture was sufficiently mixed. Thereafter, the mixture was boiled for 10 minutes and then cooled by flowing water, followed by measurement of the absorbance at a wavelength of 620 nm. Based on the measured absorbance and the calibration curve, the total amount of saccharides was determined. The calibration curve was prepared using a D-glucose standard solution.

Experiment 3-2: Results and Discussion

Table 3 shows the content of glucose residues having each linkage mode, determined by the methylation analysis of

On Relationship of Linkage Mode with Viscosity and Coloration

Based on the results shown in Table 3, regarding the relationship of the handleability and the coloration with the content of glucose residues having each linkage mode determined by the methylation analysis, it was thought that the contents of α-1,4-linked glucose and α-1,4,6-linked glucose have a characteristic relationship with the handleability and the coloration. More specifically, Test Samples 1, 4, and 5, which were rated as "poor" in terms of the handleability, had relatively high contents of α-1,4-linked glucose (15.4%, 15.3%, and 15.6%, respectively). On the other hand, Test Samples 6 and 7, which were rated as "excellent" in terms of the handleability, but were rated as "high" in terms of the coloration, indicating the presence of a problem in the coloration, tended to have relatively low contents of α-1,4-linked glucose (8.2% and 6.3%, respectively). Further, the content of α-1,4,6-linked glucose tended to be relatively high in Test Samples 1, 4, and 5, but tended to be relatively low in Test Samples 6 and 7. From the above results, it was thought that a sample with poor handleability has no problem in the coloration, and has a high content of α-1,4-linked glucose, and that a sample with good handleability and problematic coloration tends to have low contents of both α-1,4-linked glucose and α-1,4,6-linked glucose.

From a comprehensive point of view, taking also the Example 1 and the Comparative Example 1 described later into account, it was thought that, in a saccharide composition obtained by a cyclic-tetrasaccharide-forming reaction in which α-isomaltosylglucosaccharide-forming enzyme and α-isomaltosyltransferase are allowed to act on a partial starch hydrolyzate, a problem generally tends to occur in the handleability while causing no problem in the coloration when the content of α-1,4-linked glucose is over 15%, or the content of α-1,4,6-linked glucose is 6% or higher, except in cases where a starch debranching enzyme is allowed to act in parallel with the cyclic-tetrasaccharide-forming reaction, such as the cases of Test Samples 2, 3, and 8. On the other hand, it was thought that, when the content of α-1,4-linked glucose is 9% or lower, the content of α-1,4,6-linked glucose exhibits a value of less than 6%, so that the saccharide composition tends to have a problem in the coloration while having no problem in the handleability.

In contrast, in Test Samples 2, 3, and 8, which were obtained by a process in which a starch debranching enzyme was allowed to act in parallel with the cyclic-tetrasaccharide-forming reaction, the content of α-1,4-linked glucose was over 9% and 15% or lower, and the content of α-1,4, 6-linked glucose was less than 6%. Correspondingly to these results, Test Samples 2, 3, and 8 had neither a problem in the handleability nor a problem in the coloration. From the above results, as well as the results of Example 1 and Comparative Example 1 described later, it was found that a cyclic-tetrasaccharide-containing starch syrup having neither a problem in the handleability nor a problem in the coloration can be obtained in the case where the content of α-1,4-linked glucose is 15% or lower even when it is over 9%, and where the content of α-1,4,6-linked glucose is less than 6%. As shown in Table 1 above, the viscosities of Test Samples 2, 3, and 8 were 26.4 Pa·s, 18.1 Pa·s, and 32.4 Pa·s, respectively. These values were remarkably lower than 45.6 Pa·s, the viscosity of Test Sample 1, which was produced by a conventional production method. Further, since Test Samples 4 and 5, whose viscosities were 36.1 Pa·s and 38.3 Pa·s, respectively, were rated as "poor" (x) in terms of the handleability, it was judged that a viscosity of 35.0 Pa·s or lower is preferred, and a viscosity of 33.0 Pa·s or lower is more preferred, for the saccharide composition according to the present invention.

The above discovery, obtained by the combined use of a starch debranching enzyme in the cyclic-tetrasaccharide-forming reaction employing α-isomaltosylglucosaccharide-forming enzyme and α-isomaltosyltransferase, can be said to be a completely novel, epoch-making discovery uniquely made by the present inventors.

On Relationship of Handleability and Coloration with Production Method

Regarding the relationship with the production method, a cyclic-tetrasaccharide-containing starch syrup whose content of α-1,4-linked glucose is over 9% and 15% or lower, and whose content of α-1,4,6-linked glucose is less than 6%, which shows good handleability and low coloration, can be efficiently obtained by allowing a starch debranching enzyme to act during the process of the cyclic-tetrasaccharide-forming reaction, as is evident from the results in Tables 1, 2, and 4. On the other hand, in the case where α-amylase, which is an endo-type amylase, was allowed to act without allowing a starch debranching enzyme to act (Test Sample 4), the case where a starch debranching enzyme was allowed to act after the cyclic-tetrasaccharide-forming reaction (Test Sample 5), and the cases where glucoamylase, which is an exo-type amylase, was allowed to act together with a starch debranching enzyme (Test Samples 6 and 7), a cyclic-tetrasaccharide-containing saccharide composition (starch syrup) whose contents of α-1,4-linked glucose and α-1,4, 6-linked glucose are within the ranges described above could not be obtained. It was thus thought that achievement of the object of the present invention is difficult in cases where an endo-type amylase alone is allowed to act without allowing a starch debranching enzyme to act, cases where a starch debranching enzyme is allowed to act, but the timing of the action is after the completion of the cyclic-tetrasaccharide-forming reaction, and cases where an exo-type amylase is allowed to act together with a starch debranching enzyme.

On Relationship of Content of Carbohydrates Having Medium Degree of Polymerization, with Handleability and Coloration Based on the results shown in Table 3 obtained by determining the content of carbohydrates with a medium degree of polymerization (with a degree of polymerization of 4 to 13), Test Samples 2, 3, and 8, which had no problem in either handleability or coloration, showed remarkably higher contents, over 37% by mass, of carbohydrates with a degree of polymerization of 4 to 13 (excluding, however, cyclic tetrasaccharides, and branched cyclic tetrasaccharides containing one or two glucose molecules linked to a cyclic tetrasaccharide) compared to other cases. Therefore, the content of carbohydrates with a degree of polymerization of 4 to 13 was thought to be involved in the good handleability and the low coloration, which are incompatible characteristics. It was thus thought that not only the contents of glucose residues having the above-described particular linkage modes, but also the content of carbohydrates with a degree of polymerization of 4 to 13 can be used as indices indicating whether or not a cyclic-tetrasaccharide-containing saccharide composition has good handleability and low coloration.

Experiment 4: Other Analyses and Evaluations

Based on the above-described Experiments 1, 2, and 3, it was found that Test Samples 2, 3, and 8 enable achievement of the object of the present invention from the viewpoint of their good handleability and low coloration. In Experiment 4, evaluation tests were carried out on the absence of precipitation of carbohydrates during storage, and on the low calorie property, as other issues. In addition, evaluation of the dietary fiber property was carried out.

Experiment 4-1: Materials

The Test Samples 2, 3, and 8 prepared in Experiment 1-1-2 were used as the subjects to be evaluated.

Experiment 4-2: Methods

Evaluation of Crystal Precipitation Property During Storage

Equal amounts of Test Samples 2, 3, and 8, and, as a control, the same maltotetraose-containing starch syrup as in Experiment 2, were separately placed in glass beakers, and kept at 4° C. for 1 week. The presence or absence of precipitates was then visually evaluated.

Calculation of Energy Value

As described later in the reference test, the energy conversion factor of cyclic tetrasaccharide was determined to be 0 kcal/g. On the other hand, the cyclic-tetrasaccharide-containing starch syrup prepared in Experiment 1 is assumed to be digested in the living body, resulting in conversion of the coexisting carbohydrate and the branched-structure moiety of the branched cyclic tetrasaccharide to glucose, to become an energy source. Based on the above assumption, the total cyclic tetrasaccharide content (% by mass) of each of Test Samples 2, 3, and 8 was subtracted from 100% by mass, and the resulting value was multiplied by the energy conversion factor of glucose, 4 kcal/g, to determine the energy value of each test sample.

Measurement of Dietary Fiber Content

As a solid, 100 mg of each of Test Samples 2, 3, and 8 was precisely taken, and then subjected to α-amylase digestion, protease digestion, and amyloglucosidase digestion using a commercially available dietary fiber assay kit (trade name, "Dietary Fiber Total Assay Control Kit"; manufactured by Sigma. Kanagawa, Japan) according to the method described in Section 8, Dietary fiber, (2) High-performance liquid chromatography (Enzyme-HPLC method), in "Methods for analyzing nutritional components, etc. (Methods described in Appendix 1-3 of Nutrition Labeling Standard)" in Nutrition Labeling Standard (Notification No. 146 of Ministry of Health, Labour, and Welfare, May 1996)", followed by desalting and concentration according to conventional methods, and then adjustment of the volume to 25 mL. The solution after the treatment was subjected to HPLC under the following conditions, to determine the peak area ratio of the other component (that is, dietary fiber) relative to that of glucose in the solution after the treatment.

HPLC Conditions

Column: two "TSKgel G2500PWXL" (7.8 mm (inner diameter)×300 mm (length); manufactured by Tosoh Corporation, Tokyo, Japan) columns connected in series
Eluent: Ultrapure water
Sample saccharide concentration: 0.8% by mass
Column temperature: 80° C.
Flow rate: 0.5 mL/minute
Detection: differential refractive index
Injection volume: 20 μL
Analysis time: 50 minutes
The apparatuses and conditions not described here were the same as those in the saccharide composition analysis shown in Experiment 1-2.

Subsequently, the amount of glucose (mg) contained in each treated solution was quantified by the ordinary glucose oxidase method, and the quantified value was multiplied by the peak area ratio of the other component (that is, dietary fiber) relative to that of glucose in the treated solution determined as described above, to calculate the amount of dietary fiber (mg) contained in the treated solution. Based on this result and the initial mass of the solid (100 mg) in each test sample, the dietary fiber content (% by mass) in the test sample was determined.

Experiment 4-3: Results and Discussion

The results are shown in Table 4.

TABLE 4

| Test sample No. | 2 | 3 | 8 |
|---|---|---|---|
| Crystal precipitation property*[1] | ◯ | ◯ | ◯ |
| Energy value (kcal/g-dry solid) | 2 | 2 | 2 |
| Dietary fiber content (% by mass) | 73 | 74 | 74 |

*[1]"◯" represents that no precipitation of crystals was found, similarly to the control.

As can be seen in Table 4, no precipitation of crystals occurred in Test Samples 2, 3, and 8 under the above-described conditions, similarly to the case of the control maltotetraose-containing starch syrup. Crystallization of a cyclic tetrasaccharide easily occurs. For example, as shown in Experiment 30 of Patent Document 1, a cyclic tetrasaccharide having a purity of 98% by mass easily causes precipitation of crystals when it is prepared as an aqueous solution with a solid concentration of 50% by mass. In view of this, it can be said that Test Samples 2, 3, and 8 sufficiently have the property that precipitation of crystals hardly occurs even as a highly concentrated aqueous solution, which property is required for starch syrups. In Test Samples 2, 3, and 8, the energy value was 2 kcal/g. Based on the fact that a carbohydrate completely digested and absorbed has an energy value of 4 kcal/g, it can be said that the low calorie property of the test samples can be sufficiently appealed. The dietary fiber content was also at a relatively high level as expected. Thus, Test Samples 2, 3, and 8 could be confirmed to be cyclic-tetrasaccharide-containing saccharide compositions that enable achievement of all objects in the present invention.

Reference Test: Calculation of Energy Conversion Factor of Cyclic Tetrasaccharide 1. Background and Object A preliminary evaluation has revealed that a cyclic tetrasaccharide orally ingested into a human body reaches the large intestine without being digested or absorbed. On the other hand, whether or not the cyclic tetrasaccharide is fermented by enterobacteria has been unclear. Calculation of the energy conversion factor of a carbohydrate that completely reaches the large intestine without being digested or absorbed needs to be carried out by quantitatively determining the degree of fermentation based on comparison with a material which is known not to be digested or absorbed but is known to be completely fermented by enterobacteria, and whose energy conversion factor is known, such as a fructooligosaccharide (energy conversion factor, 2 kcal/g) (Non-patent Document 3). It is known that, when a carbohydrate that undergoes fermentation by enterobacteria is orally ingested, hydrogen gas in the exhaled breath tends to increase depending on the amount of the carbohydrate ingested. Thus, for example, by comparing the total amount of hydrogen gas generated in the exhaled breath by ingestion of fructooligosaccharide with the total amount of hydrogen gas generated in the exhaled breath by ingestion of the carbohydrate to be evaluated, the degree of fermentation of the carbohydrate to be evaluated can be determined as the percentage relative to that of fructooligosaccharide. By multiplying the energy conversion factor of fructooligosaccharide, 2 kcal/g, by the percentage determined, the energy conversion factor of the subject to be evaluated can be calculated.

Based on such a background, the energy conversion factor of a cyclic tetrasaccharide was calculated using the following materials and methods.

2. Materials

As a test substance, a crystal preparation of a cyclic tetrasaccharide prepared according to the method described in Patent Document 1 was used. As a control substance, fructooligosaccharide (trade name, "Meioligo"; manufactured by Meiji Co., Ltd., Tokyo, Japan) was used.

3. Methods and Results

Subjects

A total of 13 healthy adults including males and females were selected as subjects.

Ingestion of Food, Test Substance, and Control Substance, and Collection of Exhaled Breath By 9 PM on the day before the test, all subjects were allowed to have a meal of the same menu containing neither dietary fiber nor fermentable materials. At 7 AM on the day of the test, each subject was confirmed to be in good physical condition, and allowed to collect his/her own end-tidal air using the breath-collecting apparatus described below. Thereafter, the subject was allowed to ingest, within 2 minutes, a liquid prepared by dissolving a test substance in an amount of 5 g on a solid basis in 100 mL of water. Until 14 hours have passed after the ingestion, the end-tidal air was similarly collected at hourly intervals. In this period, a meal of the same menu containing neither dietary fiber nor fermentable materials was provided every 3 hours. Each subject was allowed to ingest or skip the meal, and to choose the amount of ingestion, according to his/her arbitrarily decision. Further, particular beverage articles containing neither dietary fiber nor fermentable materials were constantly provided, and each subject was allowed to ingest the articles at any time and to choose the amount of ingestion according to his/her arbitrarily decision. The subject was also allowed to add sugar to the articles ad libitum.

One month after the test of ingestion of the test substance, each subject was similarly allowed to ingest a control substance instead of the test substance, and to collect his/her exhaled breath.

Measurement of Hydrogen Gas Concentration in Exhaled Breath

For the collection of the exhaled breath, a commercially available breath-collecting apparatus (trade name, "end-tidal air (alveolar air) collection system"; manufactured by Laboratory for expiration biochemistry nourishment metabolism Co., Ltd., Nara. Japan was used. The hydrogen gas concentration in the collected exhaled breath was measured using a commercially available breath gas analyzer (trade name, "Breath Gas Analyzer BGA-1000D"; manufactured by Laboratory for expiration biochemistry nourishment metabolism Co., Ltd., Nara, Japan).

Calculation of Energy Conversion Factor of Cyclic Tetrasaccharide Based on Measurement Result of Hydrogen Gas Concentration in Exhaled Breath The amount of hydrogen gas discharged into the exhaled breath of each subject was evaluated by preparing a graph by taking the collection time of the exhaled breath along the abscissa and the hydrogen gas concentration along the ordinate, plotting the gas concentration in the exhaled breath measured at each time during the test in the graph, and then measuring the Area Under Curve (AUC) of the curve drawn by the plotting. The percentage of the AUC of the test substance relative to the AUC of the control substance was determined for each subject, and the average was calculated therefrom. The average of the percentage was multiplied by the energy conversion factor of fructooligosaccharide, 2 kcal/g, and the calculated value was evaluated in accordance with the standard in the art, in which an energy conversion factor is expressed as the value obtained by rounding to the nearest integer (Non-patent Document 3). As a result, the energy conversion factor of cyclic tetrasaccharide was determined to be 0 kcal/g.

Example 1

Cyclic-Tetrasaccharide-Containing Starch Syrups

Example 1-1

As a raw material, a potato starch-liquefied liquid with a DE of 5 and a solid concentration of 20% by mass was used. To the raw material, 2.5 units of a cyclic-tetrasaccharide-forming enzyme (derived from *Bacillus globisporus* (FERM BP-7143), manufactured by Hayashibara Co., Ltd., Okayama, Japan) per 1 g of the raw-material solid, 1.2 units of CGTase (derived from *Geobacillus stearothermophilus*, manufactured by Hayashibara Co., Ltd., Okayama, Japan) per 1 g of the raw-material solid, and 300 units of isoamylase (derived from *Pseudomonas amyloderamosa*, manufactured by Hayashibara Co., Ltd., Okayama, Japan) per 1 g of the raw-material solid were added, and the resulting mixture was kept at pH 6.0 at 50° C. for 48 hours to carry out cyclic-tetrasaccharide-forming reaction. Thereafter, the reaction solution was kept at 95° C. for 30 minutes to stop the reaction, and then cooled to normal temperature, followed by filtration, desalting using H-type and OH-type ion-exchange resins, decoloration using activated carbon, and then concentration to a solid concentration of 73% by mass using an evaporator according to conventional methods, to obtain a cyclic-tetrasaccharide-containing starch syrup of the present invention (Example 1-1).

Example 1-2

The same operation as in the preparation of the cyclic-tetrasaccharide-containing starch syrup of Example 1-1 was carried out except that, after performing the cyclic-tetrasaccharide-forming reaction under the conditions described above and stopping the reaction, 5 units of α-amylase (trade name, "NEO-Spitase PK-6/R"; manufactured by Nagase ChemteX Corporation, Osaka, Japan) per 1 g of the raw-material solid was added followed by allowing the reaction to proceed at 80° C. for 2 hours and keeping the resulting reaction solution at 95° C. for 30 minutes to stop the reaction, for the purpose of finishing. By this, a cyclic-tetrasaccharide-containing starch syrup of the present invention (Example 1-2) was obtained.

Example 1-3

The same operation as in the preparation of the cyclic-tetrasaccharide-containing starch syrup of Example 1-1 was carried out except that, in the cyclic-tetrasaccharide-forming reaction, the amounts of the cyclic-tetrasaccharide-forming enzyme, CGTase, and isoamylase added were set to 1 unit, 0.5 unit, and 250 units, respectively, per 1 g of the raw-material solid, and that α-amylase was added similarly to Example 1-2 after stopping the cyclic-tetrasaccharide-forming reaction, to obtain a cyclic-tetrasaccharide-containing starch syrup of the present invention (Example 1-3).

Comparative Example 1

Comparative Example 1-1

The same operation as in the case of Example 1-1 was carried out except that the addition of isoamylase was omitted in the preparation conditions for the cyclic-tetrasaccharide-containing starch syrup of Example 1-1, and that 10 units of the α-amylase used for the preparation of the cyclic-tetrasaccharide-containing starch syrup in Example 1-2 per 1 g of the raw-material solid was added instead of the isoamylase, to obtain a cyclic-tetrasaccharide-containing starch syrup outside the scope of the present invention (Comparative Example 1-1).

Comparative Example 1-2

The same operation as in the case of Example 1-1 was carried out except that the amount of isoamylase added was changed to 200 units per 1 g of the raw-material solid in the preparation conditions for the cyclic-tetrasaccharide-containing starch syrup of Example 1-1, and that 2 units of the α-amylase used in Example 1-2 and 0.2 unit of the glucoamylase used in Experiment 1 per 1 g of the raw-material solid were added upon the addition of the cyclic-tetrasaccharide-forming enzyme, to obtain a cyclic-tetrasaccharide-containing starch syrup outside the scope of the present invention (Comparative Example 1-2).

Each of the cyclic-tetrasaccharide-containing starch syrups obtained in Example 1 (Examples 1-1, 1-2, and 1-3) and Comparative Example 1 (Comparative Examples 1-1 and 1-2) was subjected to analysis and evaluation according to the following: the total cyclic tetrasaccharide content analysis, the saccharide composition analysis, and the water activity analysis shown in Experiment 1-2; the evaluation of the handleability resulting from the viscosity and the evaluation of the coloration shown in Experiment 2-2; the methylation analysis and the measurement of the content of carbohydrates with a medium degree of polymerization shown in Experiment 3-1; and the calculation of the energy value shown in Experiment 4-2. The results of the analysis and evaluation are shown below in Table 5, together with a summary of the preparation method for each cyclic-tetrasaccharide-containing starch syrup.

TABLE 5

| | | | Test sample No. | | | |
|---|---|---|---|---|---|---|
| | | Example 1-1 | Example 1-2 | Example 1-3 | Comparative Example 1-1 | Comparative Example 1-2 |
| Timing of addition, and amount (units) of enzyme used[*1] | Cyclic-tetrasaccharide-forming enzyme | 2.5 | 2.5 | 1 | 2.5 | 2 5 |
| | CGTase (from the beginning) | 1.2 | 1.2. | 0.5 | 1.2 | 1.2 |
| | Isoamylase (from the beginning) | 300 | 300 | 250 | — | 200 |
| | α-Amylase (after the completion of the reaction) | — | 5 | 5 | — | — |
| | α-Amylase (from the beginning) | — | — | — | 10 | 2 |
| | Glucoamylase (from the beginning) | — | — | — | — | 0.2 |
| Total cyclic tetrasaccharide content (% by mass) | | 50 | 50 | 38 | 48 | 50 |
| Saccharide composition[*2] (% by mass) | Cyclio tetrasaccharide | 35 | 35 | 26 | 32 | 35 |
| | DP1 + DP2 | 10 | 10 | 8 | 8 | 18 |
| | DP4 to DP13 | 40 | 40 | 40 | 45 | 30 |
| Content (%) of glucose residues having each linkage mode[*3] | α-1,4 | 13 | 13 | 14 | 11 | 9 |
| | α-1,4,6 | 4 | 4 | 5 | 7 | 5 |
| Viscosity (Pa · s) | | 27 | 26 | 29 | 40 | 20 |
| Handleability | | ○ | ○ | ○ | x | ○ |
| Coloration | | ○ | ○ | ○ | ○ | x |
| Water activity | | 0.86 | 0.86 | 0.87 | 0.88 | 0.86 |
| Energy value (Kcal/g-dry solid) | | 2 | 7 | 2 | 2 | 2 |

[*1]The name of each enzyme is followed by the timing of addition of the enzyme. The timing was as follows: "from the beginning" = The enzyme was added at the same time as the addition of the cyclic-tetrasaccharide-forming enzyme; "after the completion of the reaction" = The enzyme was added after stopping the reaction of the cyclic-tetrasaccharide-forming enzyme by heating the reaction solution. Each value represents the amount (units) of enzyme added per 1 g of the raw-material dry solid.

[*2]"DP1 + DP2" means the total content of glucose, maltose, and isomaltose "DP4 to 13" means the total content of carbohydrates with a degree of polymerization of 4 to 13 other than cyclic tetrasaccharides and branched cyclic tetrasaccharides comprising one or two linked glucose molecules.

[*3]Measurement results for α-1,4-linked glucose (represented as "α-1,4" in the table) and α-1,4,6-linked glucose (represented as "α-1,4,6" in the table) are shown among the contents of glucose residues having each linkage mode determined by methylation analysis.

All of the cyclic-tetrasaccharide-containing starch syrups of Examples 1-1 to 1-3 obtained were starch syrups showing both good handleability and coloration. These had the characteristics of the saccharide composition of the present invention that the total cyclic tetrasaccharide content is 38% by mass or higher, and that the content of $\alpha$-1,4-linked glucose is over 9% and 15% or lower, and the content of $\alpha$-1,4,6-linked glucose is less than 6%, in methylation analysis. Furthermore, the water activity and the viscosity were sufficiently low. Based on these characteristics, the cyclic-tetrasaccharide-containing starch syrups of Examples 1-1 to 1-3 are high-quality cyclic-tetrasaccharide-containing starch syrups with low coloration and good handleability, and hence can be widely used for uses such as foods, cosmetics, quasi-drugs, pharmaceuticals, livestock feeds, fish feeds, and fertilizers. As a result of measurement of the dietary fiber contents of the cyclic-tetrasaccharide-containing starch syrups of Examples 1-1 to 1-3 according to the measurement of the dietary fiber content shown in Experiment 4-2, all of these were found to have a dietary fiber content of 60% or higher, indicating that these cyclic-tetrasaccharide-containing starch syrups have a dietary fiber property.

On the other hand, the cyclic-tetrasaccharide-containing starch syrup obtained in Comparative Example 1-1 had a viscosity of as high as 40 Pa·s, indicating its poor handleability. Regarding components such as the saccharide composition, the content of $\alpha$-1,4,6-linked glucose was 7% according to the methylation analysis. This value was higher than those in the present invention, and consistent with the high viscosity and the poor handleability. The cyclic-tetrasaccharide starch syrup of Comparative Example 1-2 had no problem in the viscosity and the handleability. However, the content of carbohydrates with a degree of polymerization of 1 or 2 (DP1+DP2) in the saccharide composition was 18% by mass, showing a relatively high value. Therefore, this syrup showed high coloration, and the object of the present invention could not be achieved.

Example 2

Cyclic-Tetrasaccharide-Containing Saccharide Composition

The cyclic-tetrasaccharide-containing starch syrup of the present invention obtained in Example 1 (Example 1-1) was subjected to spray drying according to a conventional method, to obtain a cyclic-tetrasaccharide-containing saccharide composition of the present invention in a powder form. This product can be advantageously used as it is as a low-calorie food with which dietary fiber can be supplemented. The product may be appropriately mixed with other carbohydrates, high-intensity sweeteners, lipids, proteins, nucleic acids, amino acids, vitamins, surfactants, emulsifiers, lubricants, astringents, perfumes, pigments, and the like, to be advantageously used as a food material, cosmetic material, quasi-drug material, pharmaceutical material, livestock-feed material, fish-feed material, fertilizer material, or the like.

Example 3

Reduced Product of Cyclic-Tetrasaccharide-Containing Saccharide Composition The cyclic-tetrasaccharide-containing starch syrup of the present invention obtained in Example 1 (Example 1-2) was subjected to hydrogenation reaction in the presence of a nickel catalyst according to a conventional method, and then the reaction was stopped, followed by carrying out purification according to a conventional method, and adjusting the concentration, to obtain a reduced product of a cyclic-tetrasaccharide-containing saccharide composition of the present invention in the form of an aqueous solution. This product is useful as a food material, quasi-drug material, pharmaceutical material, or the like having a lower calorie content and showing less coloration since the coexisting carbohydrate contained in the cyclic-tetrasaccharide-containing starch syrup used as the raw material is converted to sugar alcohol. Further, because of the lower coloration, the product is especially useful as a material of cosmetics, and as a quasi-drug material for external application to the skin.

Example 4

Chiffon Cake

According to a conventional method, 150 parts by mass of egg yolk, 60 parts by mass of sugar, 54 parts by mass of milk, 54 parts by mass of salad oil, and 126 parts by mass of cake flour were mixed together, to prepare an egg yolk dough. Separately, 260 parts by mass of egg white, 68 parts by mass of sugar, and 56 parts by mass (41 parts by mass in terms of the solid) of the cyclic-tetrasaccharide-containing starch syrup of the present invention prepared in Example 1 (Example 1-1) were mixed together according to a conventional method, to prepare a meringue. The prepared egg yolk dough and meringue were homogeneously mixed together by the least possible number of times of stirring. The mixture was then poured into a chiffon cake mold, and baked until cracks of the dough turned pale brown, to obtain a chiffon cake. This recipe is the same as a common recipe for a chiffon cake except that 20% of the sugar was replaced with a solid of the cyclic-tetrasaccharide-containing starch syrup.

The chiffon cake obtained had a moist texture, exhibited mild sweetness, and had a good flavor. Compared to products obtained by ordinary recipes, the present product has a lower calorie content, so that the product can be comfortably taken. Moreover, since the product contains the cyclic-tetrasaccharide-containing starch syrup, it contains dietary fiber. The product is therefore a high-quality chiffon cake that can be expected to produce an effect that maintains and enhances health. Also in a case where the ratio of replacement of the sugar in the ordinary recipe was increased to 40%, the product had a good texture, taste, and flavor.

Example 5

Udon

According to a conventional method, 31 parts by mass of water, 4 parts by mass of salt, and 15 parts by mass of the cyclic-tetrasaccharide-containing starch syrup of the present invention prepared in Example 1 (Example 1-1) were mixed together, and the salt was dissolved completely. To the resulting mixture, 100 parts by mass of all-purpose flour was added, and the flour was sufficiently kneaded for 20 minutes or longer, to prepare an udon dough. The resulting udon dough was left to stand for 1 hour as it is, and then spread to a thickness of about 3 mm using a rolling pin. The dough was then folded and cut to a width of about 4 mm, to obtain udon.

The udon obtained was boiled in boiling water for about 15 minutes, and then exposed to cold water. After pouring a warmed soup (dashijiru) onto the udon, the udon was eaten. As a result, the udon was found to be a good-quality udon having a harmony between a soft texture, and a feeling upon passing through the throat (nodogoshi). It also had a good flavor. The product is also useful as a good-quality udon for dietary fiber supplementation that can be safely and comfortably taken. Also in a case where the amount of the cyclic-tetrasaccharide-containing starch syrup added in the above-described recipe was changed to 20 parts by mass, a good-quality udon could be similarly obtained.

Example 6

"An" (Sweet Red-Bean Paste)

In a pot, 700 parts by mass of water and 560 parts by mass of sugar were placed, and the sugar was completely dissolved by heating over an open fire. Thereafter, 1000 parts by mass of an unsweetened red-bean paste obtained by sufficiently mashing boiled red beans was fed thereto in three portions with gentle stirring. The resulting mixture was sufficiently boiled down by continuous heating over low heat. To the mixture, 320 parts by mass of the cyclic-tetrasaccharide-containing starch syrup of the present invention obtained in Example 1 (Example 1-1) was added, and the resulting mixture was further boiled down by continuous heating to achieve a Brix (solid concentration in terms of sucrose) of 58%, to obtain an "an". This recipe is the same as a common recipe for "an" except that 30% of the sugar was replaced with a solid of the cyclic-tetrasaccharide-containing starch syrup.

The "an" obtained had a rich gloss and delicate sweetness. Further, the "an" exhibited no deterioration of the shape retainability, which deterioration is normally found when the amount of sugar used for the unsweetened red-bean paste is reduced. The product showed no sharp increase in the viscosity during the production process, and its handleability during the production was good. Compared to products obtained by ordinary recipes, the present product has a lower calorie content, and the product contains dietary fiber because of the addition of the cyclic-tetrasaccharide-containing starch syrup. This product can thus be comfortably taken, and moreover, it is a high-quality sweetened red-bean paste that can be expected to produce an effect that maintains and enhances health. Further, by solidifying the obtained "an" using agar or the like, it can be made into a yokan. Also in a case where the ratio of replacement of the sugar in the ordinary recipe was increased to 70%, the product had a good texture, taste, and flavor.

Example 7

Gummy Candy

According to a conventional method, 100 parts by mass of sugar, 60 parts by mass of a malt sugar syrup (trade name, "MALTRUP"; manufactured by Hayashibara Co., Ltd., Okayama, Japan), 87 parts by mass of the cyclic-tetrasaccharide-containing starch syrup of the present invention obtained in Example 1 (Example 1-1), 18 parts by mass of gelatin, 36 parts by mass of water, 7.5 parts by mass of 50% by mass aqueous citric acid solution, 0.6 part by mass of a flavor, and an appropriate amount of a coloring agent were mixed together under heat, and the resulting mixture was boiled down to achieve a total amount of 300 parts by mass and a Brix of 80%, followed by molding the product to obtain a gummy candy. This recipe is the same as a common recipe for a gummy candy except that 60% of the malt sugar syrup was replaced with the cyclic-tetrasaccharide-containing starch syrup.

The gummy candy obtained exhibited a color and gloss completely equivalent to those of common gummy candies prepared without the replacement with a cyclic-tetrasaccharide starch syrup. Furthermore, the gummy candy obtained was a high-quality gummy candy which shows a stronger repulsion upon chewing compared to common gummy candies, has a good texture, and shows no stickiness on the surface. The product showed no sharp increase in the viscosity during the production process, and its handleability during the production was good. Compared to products obtained by ordinary recipes, the present product has a lower calorie content, and the product contains dietary fiber because of the addition of the cyclic-tetrasaccharide-containing starch syrup. This product can thus be comfortably taken, and moreover, it is a high-quality gummy candy that can be expected to produce an effect that maintains and enhances health.

Example 8

Hard Candy

According to a conventional method, 6 parts by mass of sugar, 2 parts by mass of a malt sugar syrup (trade name, "MALTRUP", manufactured by Hayashibara Co., Ltd., Okayama, Japan), 2 parts by mass of the cyclic-tetrasaccharide-containing starch syrup of the present invention obtained in Example 1 (Example 1-2), 10 parts by mass of water, and an appropriate amount of a flavor were mixed together, and the resulting mixture was sufficiently boiled down by heating at 155° C., followed by molding to obtain a hard candy. As a control for comparison, a candy was obtained by the same operation except that an indigestible glucan prepared by roasting starch in the presence of an acid, performing enzyme digestion, and removing glucose and the like generated, was used instead of the cyclic-tetrasaccharide-containing starch syrup of the present invention.

While the hard candy obtained as described above containing the cyclic-tetrasaccharide-containing starch syrup of the present invention had an amber color, the hard candy for comparison had a dark brown color. From this result, it could be confirmed that the cyclic-tetrasaccharide-containing starch syrup of the present invention shows low coloration, and hence that the syrup does not adversely affect the color of a product prepared by mixing the syrup with other materials and then heating the resulting mixture.

Compared to common hard candies, the present product has a lower calorie content, and the product contains dietary fiber because of the addition of the cyclic-tetrasaccharide-containing starch syrup. This product can thus be comfortably taken, and moreover, it is a high-quality hard candy that can be expected to produce an effect that maintains and enhances health.

Example 9

Ice Cream

According to a conventional method, 150 parts by mass of 35% fresh cream, 45 parts by mass of non-fat dry milk, 50 parts by mass of palm oil, 266 parts by mass of the cyclic-tetrasaccharide-containing starch syrup of the present invention obtained in Example 1 (Example 1-3), 2 parts by mass of locust bean gum, and 1 part by mass of sucrose fatty acid ester were mixed together to make the mixture homogeneous while warming the mixture over low heat. Subsequently, the mixture was mixed by vigorous stirring at normal temperature, and then dispensed into a container, followed by freezing at –20° C. to obtain an ice cream. This recipe is the same as a common recipe for an ice cream except that the high-fructose corn syrup was entirely replaced with the cyclic-tetrasaccharide-containing starch syrup.

Even when 3 days have passed after the ice cream obtained was frozen, the ice cream did not show the so-called shrinkage, which is a phenomenon in which a gap is formed between ice cream and its container. When 7 days have passed after the ice cream was frozen, the ice cream was removed from the container and observed. As a result, its surface was found to be very smooth, indicating that the ice cream is a good-quality ice cream. The product showed no sharp increase in the viscosity during the production process, and its handleability during the production was good. Regarding the taste, the product had a clear, refreshing sweetness. It also had a good texture and flavor. Compared to products obtained by ordinary recipes, the present product has a lower calorie content, and the product contains dietary fiber because of the addition of the cyclic-tetrasaccharide-containing starch syrup. This product can thus be comfortably taken, and moreover, it is a good-quality ice cream that can be expected to produce an effect that maintains and enhances health.

Example 10

Dorayaki Pancake (Dorayaki-No Kawa)

Twenty parts by mass of water was added to 65 parts by mass of egg, 50 parts by mass of sugar, 20 parts by mass (15 parts by mass in terms of the solid) of the cyclic-tetrasaccharide-containing starch syrup of the present invention prepared in Example 1 (Example 1-1), 5 parts by mass of honey, and 2 parts by mass of mirin, and the resulting mixture was mixed well. Subsequently, 0.6 part by mass of baking soda dissolved in 2 parts by mass of water, and 63 parts by mass of sieved wheat flour, were added to the mixture, to prepare a dough. After leaving the dough to stand for about 1 hour, the dough was baked on an iron plate, to obtain a dorayaki pancake.

The dorayaki pancake obtained was fluffy, and had a delicate sweetness. Compared to products obtained by ordinary recipes, the present product has a lower calorie content, and the product contains dietary fiber because of the addition of the cyclic-tetrasaccharide-containing starch syrup. This product can thus be comfortably taken, and moreover, it is a high-quality dorayaki pancake that can be expected to produce an effect that maintains and enhances health. Further, by sandwiching the "an" obtained in Example 6 between the dorayaki pancake, a high-quality dorayaki containing dietary fiber in both the pancake and the "an" can be prepared.

Example 11

Brown Sugar Steamed Bun

A mixture was prepared by mixing 60 parts by mass of egg, 180 parts by mass of brown sugar, 140 parts by mass (102 parts by mass in terms of the solid) of the cyclic-tetrasaccharide-containing starch syrup of the present invention prepared in Example 1 (Example 1-2), and 160 parts by mass of water together, and the mixture was warmed to about 30° C. in a water bath. With the warmed mixture, 200 parts by mass of cake flour and 5 parts by mass of sieved isupata (a kind of baking powder) were mixed, and 30 parts by mass of unroasted sesame seed oil was further added thereto, followed by mixing the resulting mixture well. The resulting dough was poured into a mold, and then steamed for 20 minutes, to obtain a brown sugar steamed bun.

The steamed bun obtained was a fluffy steamed bun having a delicate sweetness, and a good texture and taste. The steamed bun contains dietary fiber because of the addition of the cyclic-tetrasaccharide-containing starch syrup. It can thus be expected to produce an effect that enhances health.

Example 12

Orange Jelly

Two hundred parts by mass of sugar, 2.5 parts by mass of κ-carrageenan, 2.5 parts by mass of locust bean gum, 2.5 parts by mass of sodium citrate, 1 part by mass of potassium chloride, and 0.2 part by mass of acesulfame potassium were mixed together well, and placed in a pot containing 650 parts by mass of water, such that lumps were not formed. To the mixture, 140 parts by mass (102 parts by mass in terms of the solid) of the cyclic-tetrasaccharide-containing starch syrup of the present invention prepared in Example 1 (Example 1-3) was added, and water was evaporated from the resulting mixture by boiling down to 800 parts by mass. Thereafter, the mixture was cooled to about 70° C., and 200 parts by mass of an orange juice and an appropriate amount of an orange flavor were added thereto, followed by adjusting the pH to within the range of 3.2 to 4.0 using 50% aqueous citric acid solution. The resulting solution was filled into a jelly cup, and left to stand in a refrigerator to allow solidification, to obtain an orange jelly.

The jelly obtained contains dietary fiber because of the addition of the cyclic-tetrasaccharide-containing starch syrup. Moreover, the jelly had high shape retainability, and a smooth texture and a clear sweetness. Even in cases where the gelling agent was replaced with gelatin, xanthan gum, agar, pectin, or the like, syneresis was not found, and jellies having a good texture could be prepared.

Example 13

Cookie

One hundred parts by mass of unsalted butter was melted in a water bath, and 40 parts by mass of sieved sugar and 170 parts by mass of cake flour were added thereto, followed by mixing the resulting mixture. To the mixture, 20 parts by mass of egg yolk and 50 parts by mass of the cyclic-tetrasaccharide-containing starch syrup of the present invention prepared in Example 1 (Example 1-1) were added, followed by further mixing the resulting mixture, to obtain a dough. The dough obtained was left to stand in a refrigerator, and then shaped, followed by baking in an oven to obtain a cookie.

The cookie obtained had a crunchy texture. Moreover, the cookie is good for health since it contains dietary fiber because of the addition of the cyclic-tetrasaccharide-containing starch syrup. Further, by adding a vitamin, mineral, protein powder, and/or the like, a cookie that also enables nutritional supplementation can also be provided.

Example 14

Carbonated Beverage

Sixty parts by mass of the cyclic-tetrasaccharide-containing starch syrup of the present invention prepared in Example 1 (Example 1-2), 20 parts by mass of high-fructose corn syrup, 0.1 part by mass of acesulfame potassium, 0.02 part by mass of sucralose, 2 parts by mass of citric acid, and 0.5 part by mass of sodium citrate were mixed with 170 parts by mass of water, and the resulting mixture was stirred well until the materials were dissolved. An appropriate amount of a lemon flavor was added thereto, and the resulting mixture was stirred well, followed by addition of 750 parts by mass of carbonated water, to obtain a carbonated beverage.

The carbonated beverage obtained contains dietary fiber because of the addition of the cyclic-tetrasaccharide-containing starch syrup. The carbonated beverage had both a clear sweetness and an excellent body in spite of its low calorie content. Further, an easily drinkable carbonated beverage free of foreign taste and smell, having a sharp sweetness and an excellent body could be formulated also by the same recipe as described above except that the high-fructose corn syrup was not used, and that the amount of the cyclic-tetrasaccharide-containing starch syrup of the present invention (Example 1-2) was increased to 140 parts by mass (wherein the amount of water was changed to 90 parts by mass). Further, a carbonated beverage having an excellent body could be formulated even with a decreased solid content, by the same recipe as described above except that the amount of the cyclic-tetrasaccharide-containing starch syrup of the present invention (Example 1-2) was decreased to 20 parts by mass, and that the amount of acesulfame potassium for supplementing sweetness was increased to 0.15 part by mass.

Example 15

Chuhai (Shochu-Based Beverage)

Forty parts by mass of the cyclic-tetrasaccharide-containing starch syrup of the present invention prepared in Example 1 (Example 1-3), 0.1 part by mass of acesulfame potassium, 0.02 part by mass of sucralose, 4 parts by mass of citric acid, and 1 part by mass of sodium citrate were mixed with 170 parts by mass of a vodka containing 50% (v/v) alcohol (The Nikka Whisky Distilling Co., Ltd., Tokyo, Japan; WILKINSON VODKA 50°), and the resulting mixture was stirred well until the materials were dissolved. An appropriate amount of a lemon flavor was added thereto, and the resulting mixture was stirred well, followed by addition of 750 parts by mass of carbonated water, to obtain a chuhai.

Although the chuhai obtained had an alcohol content of as high as 9%, it was an easily drinkable chuhai free of the irritating smell and taste of alcohol. Moreover, in spite of the fact that the chuhai does not contain sugar, it had a strong body and a satisfying taste. A chuhai free of the irritating smell of alcohol, having a good body could be formulated also in a case where the amount of the cyclic-tetrasaccharide starch syrup of the present invention (Example 1-3) was decreased to 10 parts by mass (wherein carbonated water in the amount corresponding to the decrease in the volume was added).

Example 16

Canned Coffee

One hundred parts by mass of coffee beans of the *arabica* species were roasted to an L-value (brightness of coffee beans as measured by a color difference meter) of 18, and then pulverized, followed by extraction with hot water. One hundred fifty parts by mass of raw milk, 150 parts by mass of the cyclic-tetrasaccharide-containing starch syrup of the present invention prepared in Example 1 (Example 1-1), 200 parts by mass of water, and appropriate amounts of an emulsifier and a flavor were added to 500 parts by mass of a liquid prepared by adjusting the Brix of the coffee bean extract to 2, and then homogenization treatment was carried out. The homogenized liquid obtained was subjected to pH adjustment, and then filled into a can, followed by carrying out retort sterilization, to obtain a canned coffee.

The canned coffee obtained contains dietary fiber because of the addition of the cyclic-tetrasaccharide-containing starch syrup. The canned coffee was free of foreign taste and smell, had a clear taste, and was easily drinkable. The amount of dietary fiber can be arbitrarily adjusted by adjusting the amount of the cyclic-tetrasaccharide-containing starch syrup added. The sweetness can also be adjusted with sugar or an artificial sweetener.

INDUSTRIAL APPLICABILITY

As described above, the present invention provides a high-quality cyclic-tetrasaccharide-containing starch syrup whose viscosity and water activity are sufficiently low even when it is prepared as an aqueous carbohydrate solution with relatively high concentration (starch syrup), which starch syrup shows sufficiently low coloration, has a low calorie content, and is unlikely to cause precipitation of crystals of saccharides during storage. The present invention contributes to practical application of cyclic tetrasaccharides, which has been unsuccessful in the past in spite of the great expectation from the viewpoint of their physical properties and functions. The cyclic-tetrasaccharide-containing starch syrup of the present invention can be said to be an extremely useful invention from the industrial point of view since it is widely applicable to uses such as foods, cosmetics, quasi-drugs, pharmaceuticals, livestock feeds, fish feeds, and fertilizers.

The invention claimed is:

1. A saccharide composition comprising:
(a) a cyclic tetrasaccharide represented by cyclo {→6)-α-D-glucopyranosyl-(1→3)-α-D-glucopyranosyl-(1→6)-α-D-glucopyranosyl-(1→3)-α-D-glucopyranosyl-(1→}, and
(b) a branched cyclic tetrasaccharide comprising one or more glucose molecules linked to the cyclic tetrasaccharide,
wherein said saccharide composition has the following characteristics (1) to (3):
(1) after allowing glucoamylase and α-glucosidase to act on said saccharide composition, the content of cyclic tetrasaccharide with respect to the total solid content of the resulting saccharide composition is 38% by mass or higher, on a dry solid basis;
(2) the ratio of α-1,4-linked glucose in the total glucose residues constituting the saccharide composition in methylation analysis is over 9% and 15% or lower, and (3) the ratio of $\alpha$-1,4,6-linked glucose in the total glucose residues constituting the saccharide composition in methylation analysis is less than 6%.

2. The saccharide composition according to claim 1, further having the following characteristic (4):

(4) the content of the cyclic tetrasaccharide with respect to the total solid content in the saccharide composition is 25% by mass or higher, on a dry solid basis.

3. The saccharide composition according to claim 2, further having the following characteristics (5) and (6):

(5) the saccharide composition comprises carbohydrate with a degree of polymerization of 1 or 2 at a total content of 16% by mass or lower, on a dry solid basis with respect to the total solid content; and (6) the saccharide composition comprises carbohydrate with a degree of polymerization of 4 to 13 other than the cyclic tetrasaccharide and the branched cyclic tetrasaccharide comprising one or two glucose molecules linked to the cyclic tetrasaccharide, at a total content of over 37% by mass, on a dry solid basis with respect to the total solid content.

4. The saccharide composition according to claim 1, wherein an aqueous solution of the saccharide composition at a solid concentration of 73% by mass has a viscosity of 35 Pa·s or lower at 15° C.

5. The saccharide composition according to claim 1, wherein an aqueous solution of the saccharide composition at a solid concentration of 73% by mass has a water activity of less than 0.88.

6. A reduced product of the saccharide composition according to claim 1.

7. A composition comprising: the saccharide composition according to claim 1 and/or a reduced product of the saccharide composition according to claim 1; and another material.

8. An aqueous solution of (i) the saccharide composition according to claim 1, (ii) a reduced product of the saccharide composition according to claim 1, or (iii) composition comprising (i) and/or (ii) and another material.

9. The composition according to claim 8, having a solid concentration of 70% by mass or higher.

10. The saccharide composition according to claim 1, as a food, food material, cosmetic material, quasi-drug material, pharmaceutical material, livestock-feed material, fish-feed material, or fertilizer material.

11. A method of producing the saccharide composition according to claim 1, comprising the steps of:

allowing $\alpha$-isomaltosylglucosaccharide-forming enzyme and $\alpha$-isomaltosyltransferase to act on a partial starch hydrolyzate, to produce the cyclic tetrasaccharide (Step 1); and purifying and collecting the resulting enzyme reaction product containing the cyclic tetrasaccharide (Step 2); wherein a starch debranching enzyme is also allowed to act in Step 1;

with the proviso that the method includes no step of allowing an exo-type amylase having actions of producing monosaccharides or disaccharides to act.

12. The method of producing the saccharide composition according to claim 11, wherein isoamylase or pullulanase is used as the starch debranching enzyme.

13. The method of producing the saccharide composition according to claim 11, wherein cyclomaltodextrin glucanotransferase is also allowed to act in Step 1.

14. A method of producing the reduced product of the saccharide composition according to claim 6, comprising the steps of:

allowing $\alpha$-isomaltosylglucosaccharide-forming enzyme and $\alpha$-isomaltosyltransferase to act on a partial starch hydrolyzate, to produce the cyclic tetrasaccharide (Step 1); and purifying and collecting the resulting enzyme reaction product containing the cyclic tetrasaccharide (Step 2); wherein a starch debranching enzyme is also allowed to act in Step 1;

with the proviso that the method includes no step of allowing an exo-type amylase having actions of producing monosaccharides or disaccharides to act; and the method comprises a step of hydrogenation after Step 1, but before the collection in Step 2.

15. The saccharide composition according to claim 1, further having the following characteristics (5) and (6):

(5) the saccharide composition comprises carbohydrate with a degree of polymerization of 1 or 2 at a total content of 16% by mass or lower, on a dry solid basis with respect to the total solid content; and (6) the saccharide composition comprises carbohydrate with a degree of polymerization of 4 to 13 other than the cyclic tetrasaccharide and the branched cyclic tetrasaccharide comprising one or two glucose molecules linked to the cyclic tetrasaccharide, at a total content of over 37% by mass, on a dry solid basis with respect to the total solid content.

16. A method of producing the saccharide composition according to claim 2, comprising the steps of:

allowing $\alpha$-isomaltosylglucosaccharide-forming enzyme and $\alpha$-isomaltosyltransferase to act on a partial starch hydrolyzate, to produce the cyclic tetrasaccharide (Step 1); and purifying and collecting the resulting enzyme reaction product containing the cyclic tetrasaccharide (Step 2); wherein a starch debranching enzyme is also allowed to act in Step 1;

with the proviso that the method includes no step of allowing an exo-type amylase having actions of producing monosaccharides or disaccharides to act.

17. A method of producing the saccharide composition according to claim 3, comprising the steps of:

allowing $\alpha$-isomaltosylglucosaccharide-forming enzyme and $\alpha$-isomaltosyltransferase to act on a partial starch hydrolyzate, to produce the cyclic tetrasaccharide (Step 1); and purifying and collecting the resulting enzyme reaction product containing the cyclic tetrasaccharide (Step 2); wherein a starch debranching enzyme is also allowed to act in Step 1;

with the proviso that the method includes no step of allowing an exo-type amylase having actions of producing monosaccharides or disaccharides to act.

18. A method of producing the saccharide composition according to claim 4, comprising the steps of:

allowing $\alpha$-isomaltosylglucosaccharide-forming enzyme and $\alpha$-isomaltosyltransferase to act on a partial starch hydrolyzate, to produce the cyclic tetrasaccharide (Step 1); and purifying and collecting the resulting enzyme reaction product containing the cyclic tetrasaccharide (Step 2); wherein a starch debranching enzyme is also allowed to act in Step 1;

with the proviso that the method includes no step of allowing an exo-type amylase having actions of producing monosaccharides or disaccharides to act.

19. A method of producing the saccharide composition according to claim 5, comprising the steps of:

allowing α-isomaltosylglucosaccharide-forming enzyme and α-isomaltosyltransferase to act on a partial starch hydrolyzate, to produce the cyclic tetrasaccharide (Step 1); and purifying and collecting the resulting enzyme reaction product containing the cyclic tetrasaccharide (Step 2); wherein a starch debranching enzyme is also allowed to act in Step 1;

with the proviso that the method includes no step of allowing an exo-type amylase having actions of producing monosaccharides or disaccharides to act.

* * * * *